US007968554B2

(12) United States Patent
Bartkovitz et al.

(10) Patent No.: US 7,968,554 B2
(45) Date of Patent: Jun. 28, 2011

(54) PYRAZOLO[3,4-D]PYRIMIDINE DERIVATIVES

(75) Inventors: David Joseph Bartkovitz, Nutley, NJ (US); Xin-Jie Chu, Livingston, NJ (US); Kin-Chun Luk, North Caldwell, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 446 days.

(21) Appl. No.: 12/175,562

(22) Filed: Jul. 18, 2008

(65) Prior Publication Data

US 2009/0048274 A1 Feb. 19, 2009

Related U.S. Application Data

(60) Provisional application No. 60/955,653, filed on Aug. 14, 2007.

(51) Int. Cl.
*C07D 487/04* (2006.01)
*A61K 31/519* (2006.01)
*A61P 35/00* (2006.01)

(52) U.S. Cl. ..................... 514/262.1; 544/262
(58) Field of Classification Search .............. 544/262; 514/262.1
See application file for complete search history.

(56) References Cited

U.S. PATENT DOCUMENTS

| 5,985,853 | A | 11/1999 | Laugraud et al. |
|---|---|---|---|
| 2001/0020030 | A1 | 9/2001 | Stewart et al. |
| 2004/0097485 | A1 | 5/2004 | Burkitt et al. |
| 2005/0020619 | A1 | 1/2005 | Betschmann et al. |
| 2005/0026944 | A1 | 2/2005 | Betschmann et al. |
| 2005/0043347 | A1 | 2/2005 | Betschmann et al. |
| 2005/0256154 | A1 | 11/2005 | Luk et al. |

FOREIGN PATENT DOCUMENTS

| WO | WO96/32399 | 10/1996 |
|---|---|---|
| WO | WO99/62890 | 12/1999 |
| WO | WO00/42042 | 7/2000 |
| WO | WO00/71532 | 11/2000 |
| WO | WO02/44158 | 6/2002 |
| WO | WO03/082272 | 10/2003 |
| WO | WO2004/100947 | 11/2004 |
| WO | WO2005/056562 | 6/2005 |
| WO | WO2005/121107 | 12/2005 |
| WO | WO2006/068760 | 6/2006 |
| WO | WO2006/125101 | 11/2006 |
| WO | WO2007/075554 | 7/2007 |

OTHER PUBLICATIONS

Strumberg et al., Onkologie, vol. 28, pp. 101-107 (2005).
Beeram et al., J. Clin. Oncol., vol. 23, pp. 6771-6790 (2005).
Sharma et al., Cancer Res., vol. 65, pp. 2412-2421 (2005).
Ansel et al., Pharmaceutical Dosage Forms and Drug Delivery Systems, pp. 456-457 (1995).
Robins R. K., J. Am. Chem. Soc., vol. 78, p. 784 (1956).
Lyons et al., Endocrine-Related Cancer, vol. 8 pp. 219-225 (2001).
Lee et al., Current Opinion in Investigational Drugs, vol. 4(6), pp. 757-763 (2003).
Bollag et al., Current Opinion in Investigational Drugs, vol. 4(12), pp. 1436-1441 (2003).
Wilhelm, et al., Cancer Research, vol. 64, pp. 7099-7109 (2004).
Srikala et al., Mol. Cancer Ther., vol. 4(4), pp. 677-685 (2005).
Niswender et al., Journal of Biological Chem., vol. 277(32), pp. 28916-28922 (2002).
Buzko et al., Journal of Computer-Aided Molecular Design, vol. 16(2), pp. 113-127 (2002).
Bishop et al., Journal of the American Chem. Society, vol. 121(4), pp. 627-631 (1999).
Beebe et al., Cancer Research, vol. 63, pp. 7301-7309 (2003).
ASCO Annual Meeting Poster, Preclinical Development of CP-547,632, A Novel VEGFR-2 Inhibitor for Cancer Therapy, Abstract No. 473 (2002).
American Association for Cancer Research vol. 43, San Francisco, California, p. 1082 (2002).
Avruch et al., TIBS, vol. 19, pp. 279-283 (1994).
Magnuson et al., Cancer Biology, vol. 5, pp. 247-253 (1994).
SciFinder Search, Jan. 4, 2007 (36 pgs.).
Hanke et al., The Journal of Biological Chem., vol. 271, pp. 695-701 (1996).
Donnini et al., Int. J. Cancer. vol. 120, pp. 995-1004 (2006).
Schenone et al., European Journal of Med. Chem., vol. 39, pp. 939-946 (2004).
Burchat et al., Bioorganic & Medicinal Chem. Letters., vol. 16, pp. 118-122 (2006).
Bishop et a., Nature, vol. 407, pp. 395-401 (2000).
Press Release, Bayer Pharmaceuticals Corp. & Onyx Pharmaceuticals Inc., Dec. 20, 2005 (3 pgs.).

*Primary Examiner* — Susanna Moore
(74) *Attorney, Agent, or Firm* — George W. Johnston; Patricia S. Rocha-Tramaloni; Kimberly J. Prior

(57) ABSTRACT

Disclosed are novel pyrazolo[3,4-d]pyrimidine derivatives that are inhibitors of Raf kinase. These compounds and their pharmaceutically-acceptable salts and esters are anti-proliferative agents useful in the treatment or control of proliferative disorders such as solid tumors, in particular breast tumor, colon tumor, lung tumor, prostate tumor, and melanoma. Also disclosed are a composition and a unit dose formulation comprising such a compound, or a pharmaceutically-acceptable salt or ester thereof, methods for making such compounds, and methods for using such compounds, or their pharmaceutically-acceptable salts or esters, in the treatment of proliferative disorders.

18 Claims, No Drawings

PYRAZOLO[3,4-D]PYRIMIDINE DERIVATIVES

PRIORITY TO RELATED APPLICATIONS

This application claims the benefit of U.S. Provisional Application No. 60/955,653, filed Aug. 14, 2007, which is hereby incorporated by reference in its entirety.

FIELD OF THE INVENTION

The present invention is directed to novel pyrazolo[3,4-d]pyrimidine derivatives of the formula

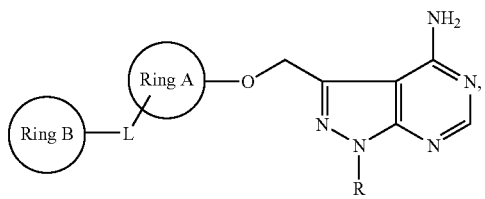

and pharmaceutically-acceptable salts and esters thereof, wherein R, Ring A, L, and Ring B are as described herein.

These compounds and their pharmaceutically-acceptable salts and esters inhibit Raf kinase and have antiproliferative activity. As such, they are useful in the treatment or control of proliferative disorders such as cancer, in particular solid tumors. This invention is also directed to a composition and a unit dose formulation comprising such a compound or a pharmaceutically-acceptable salt or ester thereof, methods of making such compounds, and methods for using such compounds, or their pharmaceutically-acceptable salts or esters, in the treatment of proliferative disorders, in particular solid tumors, and most particularly breast tumor, lung tumor, colon tumor, prostate tumor, and melanoma.

BACKGROUND OF THE INVENTION

Many disease states are characterized by uncontrolled proliferation and differentiation of cells. These disease states encompass a variety of cell types and maladies such as cancer, atherosclerosis, and restenosis. In many such disease states, kinases, important cellular enzymes that perform essential functions by regulating cell division and proliferation, appear to play a decisive role.

The molecular mechanisms and signaling pathways that regulate cell proliferation and survival are receiving considerable attention as potential targets for anticancer strategies. Recently, there has been a notable increase in efforts directed at targeting the MAPK pathway, which integrates a wide array of proliferative signals initiated by receptor tyrosine kinases (RTKs) and G protein-coupled receptors.

The MAPK signal cascade includes the G protein Ras working upstream of a core module consisting of 3 kinases: Raf, MEK1/2, and ERK1/2. Raf phosphorylates and thus activates MEK1/2, which in turn ultimately leads to the activation of ERK1/2. Raf kinase has long been considered an attractive target for drug discovery due to its importance as a potential checkpoint for cancer-related signal transduction (Strumberg and Seeber, Onkologie, 2005, 28: 101-107; Beeram et al., J. Clin. Oncol. 2005, 23: 6771-6790). The importance of the MAPK signaling cascade for the proliferation and survival of tumor cells recently increased with the discovery of activating B-Raf mutations in human tumors. Activating Raf mutations have been identified in melanoma, thyroid, colon, and other cancers (Strumberg and Seeber, Onkologie, 2005, 28: 101-107; Bollag et al., Current Opinion in Investigational Drugs, 2003, 4:1436-1441).

Therefore, in addition to a role in controlling tumors with Ras mutations and activated growth factor receptors, inhibitors of Raf kinase may harbor therapeutic potential in tumors carrying a B-Raf oncogene (Sharma et al., Cancer Res. 2005, 65: 2412-2421).

The mammalian Raf serine/threonine kinase family consists of three 68- to 74-kd proteins termed A-Raf, B-Raf, and C-Raf (Raf-1), which share highly conserved amino-terminal regulatory regions and catalytic domains at the carboxyl terminus. Raf proteins are normally cytosolic but they are recruited to the plasma membrane by the small G-protein Ras. Recruitment by Ras is an essential step for Raf activation by growth factors, cytokines, and hormones. At the membrane, Raf activation occurs through a highly complex process involving conformation changes, binding to other proteins, binding to lipids, and phosphorylation and dephosphorylation of some residues.

A variety of agents have been discovered to interfere with Raf kinase, including antisense oligonucleotides and small molecules. These inhibitors prevent the expression of Raf protein, block Ras/Raf interaction, or obstruct its kinase activity. Down regulation of B-Raf activity by siRNA or through the kinase inhibitor BAY-43-9006 leads to inhibition of the growth of melanoma cells and siRNA-mediated reduction of B-Raf led to decreased tumorigenic potential of 1205 Lu cells. Raf inhibitors that are currently undergoing clinical evaluation show promising signs of anti-cancer efficacy with a very tolerable safety profile. Clinically most advanced is the Raf inhibitor BAY 43-9006, which has recently been approved by the FDA for treatment of metastatic renal cell carcinoma with additional phase III clinical testing for treatment of other cancers.

Despite the progress that has been made, the search continues for low molecular weight compounds that are useful for treating a wide variety of tumors and other proliferative disorders including restenosis, angiogenesis, diabetic retinopathy, psoriasis, surgical adhesions, macular degeneration, and atherosclerosis. Thus, a strong need exists to provide compositions, pharmaceuticals and/or medicaments with anti-proliferative activity. Such compositions, pharmaceuticals and/or medicaments may possess not only strong activity, but also exert diminished side effects in comparison to other anti-proliferative agents. Furthermore, the spectrum of tumors responsive to treatment with such compositions, pharmaceuticals and/or medicaments may be broad. Active ingredients of this type may be suitable in the mentioned indication as single agent, and/or in combination therapy, be it in connection with other therapeutic agents, with radiation, with operative/surgical procedures, heat treatment or any other treatment known in the mentioned indications.

SUMMARY OF THE INVENTION

The present invention relates to pyrazolo[3,4-d]pyrimidine derivatives, and pharmaceutically-acceptable salts and esters thereof, which are small molecule inhibitors of Raf kinase. These compounds are useful as selective anticancer agents.

The present invention provides at least one compound of the formula

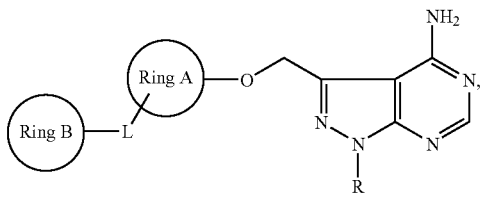

or a pharmaceutically-acceptable salt or ester thereof, wherein R, Ring A, L, and Ring B are as described herein.

DETAILED DESCRIPTION OF THE INVENTION

The term "alkenyl", as used herein, refers to a straight- or branched-chain hydrocarbon group having at least one double bond and from 2 to 6, preferably 2 to 4, carbon atoms. Examples of "alkenyl groups" are vinyl(ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The terms "alkoxy" and "alkoxyl", as used herein, each refer to a group in which an alkyl (as defined below) is attached to an oxygen atom. The term "lower alkoxy" refers to a group in which a lower alkyl (as defined below) is attached to an oxygen atom. Typical lower alkoxy groups include methoxy, ethoxy, isopropoxy or propoxy, butyloxy and the like. Further included within the meaning of alkoxy are alkoxy substituted by alkoxy, e.g. ethoxy ethoxy, methoxy ethoxy, methoxy ethoxy ethoxy and the like and substituted alkoxy side chains, e.g., dimethylamino ethoxy, diethylamino ethoxy and the like.

The term "alkyl", as used herein, refers to a straight- or branched-chain saturated hydrocarbon group having from 1 to about 20 carbon atoms, and, in certain embodiments, from 1 to about 7 carbon atoms. The term "lower alkyl" refers to an alkyl group having from 1 to 6 carbon atoms, and, in certain embodiments, from 1 to 4 carbon atoms. Examples of alkyl groups include, but are not limited to, methyl, ethyl, n-propyl, i-propyl, n-butyl, s-butyl, t-butyl, n-pentyl, and s-pentyl.

The term "alkynyl", as used herein, refers to a straight- or branched-chain hydrocarbon group having at least one triple bond and from 2 to 6, preferably 2 to 4, carbon atoms. Examples of "alkynyl groups" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "aryl", as used herein, refers to a monocyclic or bicyclic aromatic hydrocarbon group, preferably containing 6 to 10 ring carbon atoms. Preferred aryl groups include, but are not limited to, phenyl, naphthyl, tolyl, and xylyl.

The term "azole", as used herein, refers to a 5-membered heteroaryl (defined below) wherein at least one of the heteroatoms (defined below) is nitrogen. An "oxadiazole" is an azole having three heteroatoms with two being nitrogen and one being oxygen. A "triazole" is an azole having three heteroatoms with all three being nitrogen. A "tetrazole" is an azole having four heteroatoms with all four being nitrogen.

The term "carrier", as used herein, refers to a pharmaceutically inert vehicle (e.g., a solvent, suspending agent) useful in delivering an active compound, for example, a compound of Formula (I) (defined below), to a patient.

The term "cycloalkenyl", as used herein, refers to a stable monocyclic or polycyclic, non-aromatic, hydrocarbon group which is unsaturated and which contains 5 to 10 ring atoms. Examples of cycloalkenyls include, but are not limited to, cyclopentenyl or cyclohexenyl.

The term "cycloalkyl", as used herein, refers to a stable monocyclic or polycyclic, non-aromatic, saturated, hydrocarbon group containing 3 to 10 ring atoms. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane(decalin), and spiro compounds.

The term "excipient", as used herein, refers to a pharmaceutically-inert substance.

The term "halogen", as used herein, refers to fluorine, chlorine, bromine, or iodine, preferably fluorine and chlorine.

The term "heteroaryl", as used herein, refers to an aromatic mono- or bicyclic group which contains at least one heteroatom. Preferred heteroaryl groups include, but are not limited to, thienyl, furyl, indolyl, pyrrolyl, pyridinyl, pyrazinyl, oxazolyl, oxadiazolyl, thiazolyl, quinolinyl, pyrimidinyl, imidazole, triazolyl, and tetrazolyl. In the case of a bicyclic heteroaryl group, it should be understood that the ring atoms of one ring may all be carbon while the other ring may contain a heteroatom.

The term "heterocycle", as used herein, refers to 4- to 8-membered mono- or bicyclic, saturated or partially unsaturated, non-aromatic group which contains 1 to 3 "heteroatoms". The term "heteroatom", as used herein, refers to a ring atom that is nitrogen, oxygen, or sulfur. Examples of heterocycles include pyrrolidin-2-yl; pyrrolidin-3-yl; piperidinyl; morpholin-4-yl and the like. In the case of a bicyclic heterocycle, it should be understood that the ring atoms of one ring may all be carbon while the other ring may contain a heteroatom.

"$IC_{50}$" refers to the concentration of a particular compound required to inhibit 50% of a specific measured activity. $IC_{50}$ can be measured, inter alia, as described subsequently.

The term "pharmaceutically-acceptable", as used herein in reference to a compound (e.g., a carrier, a salt, an ester, etc.), means that the compound is pharmacologically acceptable and substantially non-toxic to the subject to which the particular compound is administered.

A "pharmaceutically-acceptable salt" of a compound is a conventional acid-addition salt or a base-addition salt that retains the biological effectiveness and properties of the compound and that is formed from a suitable non-toxic organic or inorganic acid or base. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, lithium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456.

A "pharmaceutically-acceptable ester" of a compound is a conventional ester of the compound which contains a hydroxyl or carboxyl group; the ester retains the biological effectiveness and properties of the compound and is capable of being cleaved in vivo (in the organism) to the corresponding active alcohol or carboxylic acid respectively.

The term "substituted", as used herein to describe any of the above chemical groups (e.g., substituted alkyl, substituted aryl, substituted heteroaryl), refers to a chemical group in which 1 to 5 hydrogen atoms, preferably 1 to 3, have been independently replaced with a substituent.

The term "unit dose formulation", as used herein, refers to a pharmaceutical preparation (e.g., tablet, capsule) comprising an active agent, for example, a compound according to Formula (I) (defined below), in stable form and capable of being administered to a patient as a single dose.

The present invention relates to a compound of Formula (I),

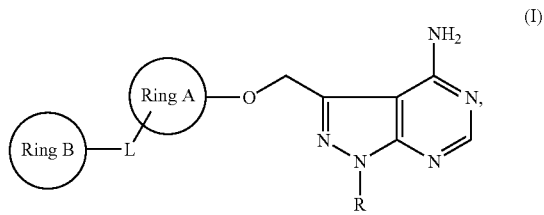

wherein
R is lower alkyl;
Ring A is selected from the group consisting of:
  heteroaryl;
  heteroaryl substituted by 1 to 5 substituents independently selected from the group consisting of: lower alkyl; halogen; hydroxyl; lower alkoxy; lower alkoxy substituted by hydroxyl or lower alkoxy; and cyano; phenyl; and
  phenyl substituted by 1 to 4 substituents independently selected from the group consisting of: lower alkyl; halogen; hydroxyl; lower alkoxy; lower alkoxy substituted by hydroxyl or lower alkoxy; and cyano;
Ring B is selected from the group consisting of:
  heteroaryl;
  heteroaryl substituted by 1 to 5 substituents selected from the group consisting of: lower alkyl; fluorinated alkyl; aryl-substituted alkyl; hydroxyl; lower alkoxy; lower alkoxy substituted by hydroxyl or lower alkoxy; halogen; and —$NR^1R^2$;
  phenyl; and
  phenyl substituted by 1 to 5 substituents selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —$NR^1R^2$;
$R^1$ and $R^2$ are each independently selected from the group consisting of hydrogen, lower alkyl, and lower alkyl substituted with hydroxyl or lower alkoxy, and $R^1$ and $R^2$, together with N, can form a 5- or 6-membered heterocyclic ring; and
L is selected from the group consisting of: a bond, —$OCH_2$—, —$CH_2O$—, —NHCO—, —CONH—, —O—, —$OCH_2CH_2$—, —$CH_2OCH_2$, —$CH_2CH_2O$—, —CF=CH—, —CH=CF—, —NH—, —$NHCH_2$—, —$CH_2NH$—, —$SCH_2$—, —$CH_2S$—, —$SOCH_2$—, —$CH_2SO$—, —$SO_2CH_2$—, —$CH_2SO_2$—, —S—, —CH=CH—, and lower alkyl;
with the proviso that, when L is a bond, Ring B is an azole substituted by 1 to 4 substituents selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —$NR^1R^2$;
or a pharmaceutically-acceptable salt or ester of such a compound.

In a preferred embodiment of the present invention, Ring A is substituted by one substituent selected from the group consisting of: lower alkyl; halogen; hydroxyl; lower alkoxy; lower alkoxy substituted by hydroxyl or lower alkoxy.

In another preferred embodiment of the present invention, when Ring A is a phenyl or a substituted phenyl, L is bonded at a position that is meta with relation to 1-alkyl-1H-pyrazolo[3,4-d]pyrimidin-3-ylmethoxy.

In another preferred embodiment of the present invention, when Ring B is a substituted heteroaryl or a substituted phenyl, Ring B is substituted by 1 or 2, substituents selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —$NR^1R^2$; wherein $R^1$ and $R^2$ are as defined above. In a particularly preferred embodiment, Ring B is 3 or 4 mono-substituted or 3,4-disubstituted wherein the substituents may be different and the substituents are preferably independently selected from the group consisting of: halogen; hydroxyl; lower alkoxy; lower alkoxy substituted with hydroxyl or lower alkoxy; —$NR^1R^2$; and —$CF_3$; with $R^1$ and $R^2$ as defined above.

In a preferred embodiment of the present invention, L is a bond and Ring B is selected from the group consisting of: substituted 1,3,4-oxadiazole; substituted 1,2,4-oxadiazole; substituted 1,2,3-triazole; substituted 1,2,4-triazole; and substituted tetrazole; wherein the substituents are independently selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —$NR^1R^2$; wherein $R^1$ and $R^2$ are as defined above. Embodiments in which Ring B is a substituted 1,3,4-oxadiazole are particularly preferred.

In another preferred embodiment, Ring A is phenyl substituted by methyl at a position that is ortho with relation to 1-alkyl-1H-pyrazolo[3,4-d]pyrimidin-3-ylmethoxy. In an especially preferred embodiment, Ring A is phenyl substituted by methyl at a position that is ortho with relation to 1-alkyl-1H-pyrazolo[3,4-d]pyrimidin-3-ylmethoxy and L is bonded to Ring A at a position that is para with relation to methyl.

In another preferred embodiment, R is methyl.

In another preferred embodiment, halogen is selected from the group consisting of Cl and F.

In another preferred embodiment, L is selected from the group consisting of —$CH_2O$—, —NHCO—, and —CONH—.

In a preferred embodiment:
Ring A is phenyl substituted by 1 to 4 substituents independently selected from the group consisting of: lower alkyl; halogen; hydroxyl; lower alkoxy; lower alkoxy substituted by hydroxyl or lower alkoxy; and cyano;
L is selected from the group consisting of —$CH_2O$—, —NHCO—, and —CONH—; and
Ring B is phenyl substituted by 1 to 5 substituents selected from the group consisting of: lower alkyl; fluorinated alkyl;

aryl-substituted alkyl; hydroxyl; lower alkoxy; lower alkoxy substituted by hydroxyl or lower alkoxy; halogen; cyano; and —NR$^1$R$^2$; with R$^1$ and R$^2$ being as defined above.

More preferably, R is methyl. Even more preferably, R is methyl and Ring B is 3 or 4 mono-substituted or 3,4-di-substituted where the two substituents may be different. Preferred substituents for Ring B are halogen, —NR$^1$R$^2$, hydroxyl, lower alkoxy, lower alkoxy substituted with hydroxyl or lower alkoxy, and —CF$_3$, with R$^1$ and R$^2$ as defined above.

In another preferred embodiment:
Ring A is selected from the group consisting of phenyl and phenyl substituted by methyl;
L is a bond; and
Ring B is a substituted azole, for example, substituted 1,3,4-oxadiazole, substituted 1,2,4-oxadiazole, substituted 1,2,3-triazole, substituted 1,2,4-triazole, and substituted tetrazole, preferably a substituted 1,3,4-oxadiazole, wherein the substituents are independently selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —NR$^1$R$^2$; wherein R$^1$ and R$^2$ are as defined above.
More preferably R is methyl. Even more preferably, R is methyl, and Ring B is substituted by lower alkyl, —NR$^1$R$^2$, hydroxyl, lower alkoxy, lower alkoxy substituted with hydroxyl or lower alkoxy, or —CF$_3$, with R$^1$ and R$^2$ as defined above. Especially preferably, R is methyl and Ring B is a 1,3,4-oxadiazole substituted as above.

Especially preferred are the following compounds:
3-(3-benzyloxy-phenoxymethyl)-1-methyl-1H-pyrazolo[3,4-d]pyrimidin-4-ylamine;
N-[3-(4-amino-1-methyl-1H-pyrazolo[3,4-d]pyrimidin-3-ylmethoxy)-4-methyl-phenyl]-3-chloro-4-(2-hydroxy-ethylamino)-benzamide;
N-[3-(4-amino-1-methyl-1H-pyrazolo[3,4-d]pyrimidin-3-ylmethoxy)-4-methyl-phenyl]-3-chloro-benzamide;
4-chloro-1-methyl-3-[2-methyl-5-(3-methyl-[1,2,4]oxadiazol-5-yl)-phenoxymethyl]-1H-pyrazolo[3,4-d]pyrimidine;
3-(5-benzyloxy-2-methyl-phenoxymethyl)-1-methyl-1H-pyrazolo[3,4-d]pyrimidin-4-ylamine;
3-(4-amino-1-methyl-1H-pyrazolo[3,4-d]pyrimidin-3-yl-methoxy)-N-(4-chloro-phenyl)-4-methyl-benzamide;
3-[5-(4-chloro-benzyloxy)-2-methyl-phenoxymethyl]-1-methyl-1H-pyrazolo[3,4-d]pyrimidin-4-ylamine;
1-methyl-3-[2-methyl-5-(5-methyl-[1,3,4]oxadiazol-2-yl)-phenoxymethyl]-1H-pyrazolo[3,4-d]pyrimidin-4-ylamine; and
3-(4-amino-1-methyl-1H-pyrazolo[3,4-d]pyrimidin-3-yl-methoxy)-N-(3-chloro-4-fluoro-phenyl)-4-methyl-benzamide; and
pharmaceutically-acceptable salts and esters of any of the foregoing compounds.

The compound of Formula (I), or the salt or ester thereof, (hereafter, collectively, "the compound of the present invention") may exist as a racemic mixture or as an isolated stereoisomer. The stereoisomer may be isolated by known separation methods, for example, by chromatography.

The compound of the present invention may exhibit tautomerism or structural isomerism. It is intended that the invention encompasses any tautomeric or structural isomeric form of the compound of the present invention, or mixtures of such forms, and is not limited to any one tautomeric or structural isomeric form depicted in Formula (I).

The compound of the present invention is useful in the treatment or control of cell proliferative disorders, in particular oncological disorders. The compound and compositions and unit dose formulations containing such a compound may be useful in the treatment or control of solid tumors, such as, for example, breast tumor, colon tumor, lung tumor, prostate tumor, and melanoma.

A therapeutically-effective amount of a compound of the present invention is an amount of the compound that is effective to prevent, alleviate or ameliorate symptoms of disease or prolong the survival of the subject being treated. The therapeutically-effective amount or dosage can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration of the compound of the present invention to adult humans weighing approximately 70 kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or, for parenteral administration, it may be given as a continuous infusion.

The present invention relates also to a process for the preparation of the compound of Formula (I). The compounds of the present invention can be prepared by any conventional means. Suitable processes for synthesizing these compounds are provided in the Examples. Generally, compounds of Formula (I) can be prepared according to the below described scheme.

1) 1-(Ethoxyethylidene)malononitrile (Aldrich) is reacted with hydrazine hydrate (Aldrich) to produce 5-amino-3-methyl-1H-pyrazole-4-carbonitrile. 5-Amino-3-methyl-1H-pyrazole-4-carbonitrile is then reacted with sulfuric acid to produce 5-amino-3-methyl-1H-pyrazole-4-carboxylic acid amide.

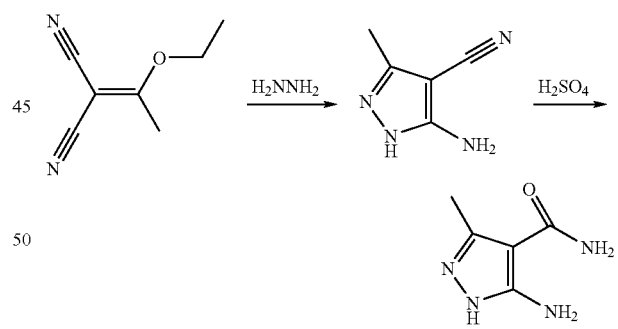

2) 5-Amino-3-methyl-1H-pyrazole-4-carboxylic acid amide is reacted with formamide (Aldrich) to produce 3-methyl-pyrazolo[3,4-d]pyrimidin-4-one.

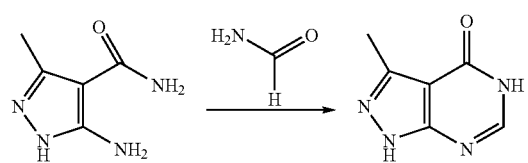

3) 3-Methyl-pyrazolo[3,4-d]pyrimidin-4-one is reacted with phosphorous oxychloride to produce 4-chloro-3-methyl-1H-pyrazolo[3,4-d]pyrimidine.

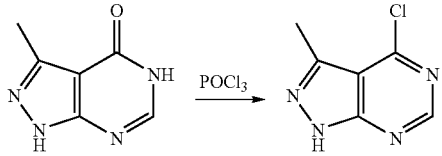

4) 4-Chloro-3-methyl-1H-pyrazolo[3,4-d]pyrimidine is reacted with RI wherein R is lower alkyl as described above and I is iodide (for example, iodomethyl available from Aldrich) to produce 1-alkyl-4-chloro-3-methyl-1H-pyrazolo[3,4-d]pyrimidine.

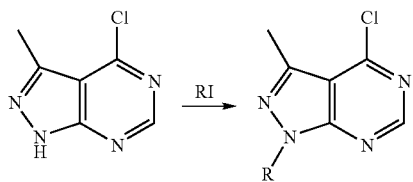

5) 1-Alkyl-4-chloro-3-methyl-1H-pyrazolo[3,4-d]pyrimidine is reacted with N-bromosuccinate (Aldrich) to produce 1-alkyl-3-bromomethyl-4-chloro-1H-pyrazolo[3,4-d]pyrimidine.

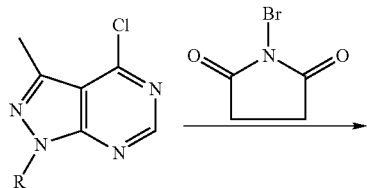

6) 1-Alkyl-3-Bromomethyl-4-chloro-1H-pyrazolo[3,4-d]pyrimidine is reacted with a compound of the formula

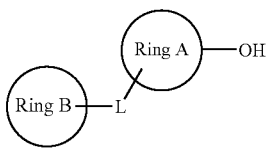

(for example, 3-benzyloxy-phenol, available from TCl) to produce a compound of the formula

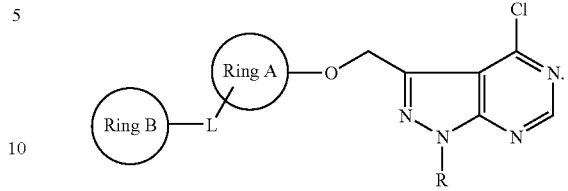

7) The compound produced in (6) is reacted with ammonia to produce a compound of Formula (I).

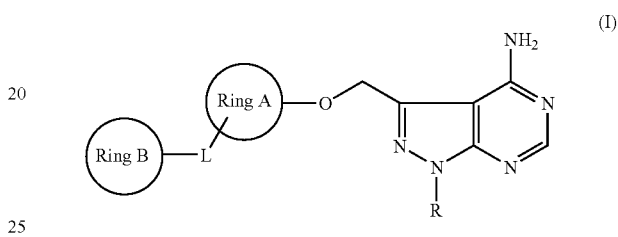

(I)

The present invention relates also to a composition and a unit dose formulation comprising the compound of the present invention. The composition and unit dose formulation comprise a therapeutically-effective amount of the compound of the present invention and a carrier. The compositions and unit dose formulation may also comprise additional accessory ingredients, for example, other excipients. Generally, from about 1 to about 99 percent of the composition or unit dose formulation consists of the compound of the present invention, preferably from about 5 to about 70 percent, and most preferably from about 10 to about 30 percent.

Lactose, corn starch or derivatives thereof, talc, stearic acids or its salts and the like can be used, for example, as carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance, no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The composition and unit dose formulation of the present invention can also comprise additional excipients, for example, preservatives, solubilizers, stabilizers, wetting agents, emulsifiers, sweeteners, colorants, flavorants, salts for use in varying osmotic pressure, buffers, masking agents, and antioxidants.

The composition and unit dose formulation of the present invention can also comprise additional therapeutically active agents.

Unit dose formulations of the present invention include those suitable for oral, nasal, topical (including buccal and sublingual), rectal, vaginal and/or parenteral administration. The formulation may be prepared by any method well known in the art of pharmacy.

Unit dose formulations of the present invention which are suitable for oral administration may be in the form of capsules, cachets, sachets, pills, tablets, lozenges (using a flavored basis, usually sucrose and acacia or tragacanth), powders, granules, elixirs, syrups, pastilles (using an inert base, such as gelatin and glycerin, or sucrose and acacia), mouth washes, and the like. The formulation may also be a solution or a suspension of the compound of the present invention in an aqueous or non-aqueous liquid. The formulation may also be an oil-in-water or water-in-oil liquid emulsion. The compound of the present invention may also be administered as a bolus, electuary or paste.

The present invention relates also to methods for preparing the composition and unit dose formulation of the present invention. Such methods comprise the step of bringing a compound of the present invention into association with a carrier and, optionally, one or more accessory ingredients. In general, the compositions and formulations of the present invention are prepared by uniformly and intimately bringing into association a compound of the present invention with a liquid carrier, a finely divided solid carrier, or both, and then, if necessary, shaping the product.

The present invention relates also to a method for treating a patient suffering from a proliferative disorder comprising the step of administering a compound of the present invention to the patient. The compound may be contained in a composition or unit dose formulation. In a preferred embodiment, the proliferative disorder is a solid tumor. In an especially preferred embodiment, the proliferative disorder is selected from the group consisting of breast tumor, lung tumor, colon tumor, prostate tumor, and melanoma.

The following examples and references are provided to aid the understanding of the present invention, the true scope of which is set forth in the appended claims.

EXAMPLE 1

5-Amino-3-methyl-1H-pyrazole-4-carboxylic acid amide

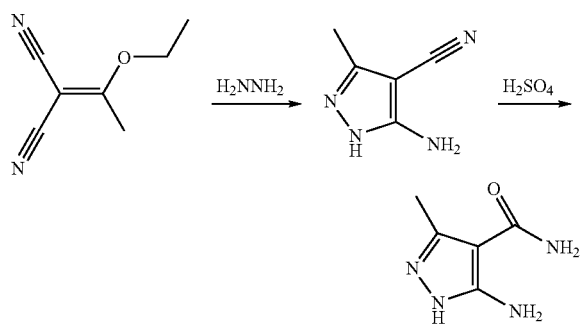

Prepared by the procedure of Robins, R. K. *J. Am. Chem. Soc.*, 1956, 78, 784.

Step 1:

1-(Ethoxyethylidene)malononitrile (25.05 g, 184.0 mmol) (Aldrich) was added in small portions to 35% (wt) hydrazine hydrate (37 mL, Aldrich). After approximately one-half of the 1-(ethoxyethylidene)-malononitrile was added, the reaction mixture was cooled in cold water and the remaining 1-(ethoxy-ethylidene)malononitrile was added at a rate such that the contents in the flask boiled gently. Upon completion of the addition, the mixture was heated at reflux for 2 hours. After cooling, the solid was filtered, washed with cold water and dried in a vacuum desiccator to give 5-amino-3-methyl-1H-pyrazole-4-carbonitrile. (Yield 15.0 g).

Step 2:

5-Amino-3-methyl-1H-pyrazole-4-carbonitrile (15.0 g, above) was added to stirred concentrated sulfuric acid (47 mL, 95%) cooled with cold water bath. After the addition, the reaction mixture was stirred at room temperature for 2 hours before it was poured with stirring into a mixture of ice and water. The precipitate was collected by filtration, washed with cold water to remove excess sulfuric acid, and dried in a vacuum desiccator to give 5-amino-3-methyl-1H-pyrazole-4-carboxylic acid amide. (Yield 19.6 g).

EXAMPLE 2

3-Methyl-pyrazolo[3,4-d]pyrimidin-4-one

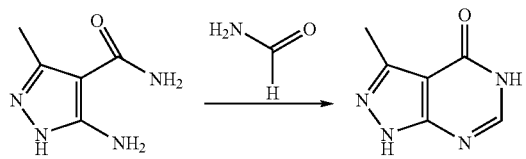

A mixture of 5-amino-3-methyl-1H-pyrazole-4-carboxylic acid amide (11.06 g, 79.0 mmol, Example 1) and formamide (60 mL, Aldrich) was heated at 180° C. for 3.5 hours. After cooling to 80° C., icy water (100 g) was added and the mixture was vigorously stirred to give a white precipitate. The precipitate was filtered and washed with cold water and then dried in a vacuum desiccator to give 3-methyl-pyrazolo[3,4-d]pyrimidin-4-one as an off-white solid. (Yield 9.07 g). This material was used in the next step (described in Example 3) without further purification.

EXAMPLE 3

4-Chloro-3-methyl-1H-pyrazolo[3,4-d]pyrimidine

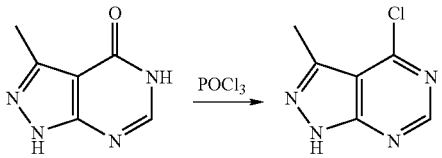

To a stirred suspension of 3-methyl-pyrazolo[3,4-d]pyrimidin-4-one (7.50 g, 50.0 mmol, Example 2) in phosphorus oxychloride (150 mL) was added diisopropylethylamine (31 mL, 175 mmol, Aldrich). The mixture was heated at reflux for 2.5 hours before the solvent was evaporated under reduced pressure. The residue was treated with ice (200 g) and made slightly basic with 4N aqueous sodium hydroxide solution and extracted with ethyl acetate (3×250 mL). The combined organic extracts were washed with water, brine, dried and concentrated to give 4-chloro-3-methyl-1H-pyrazolo[3,4-d]pyrimidine as a white solid. (Yield 6.38 g).

EXAMPLE 4

4-Chloro-1,3-dimethyl-1H-pyrazolo[3,4-d]pyrimidine

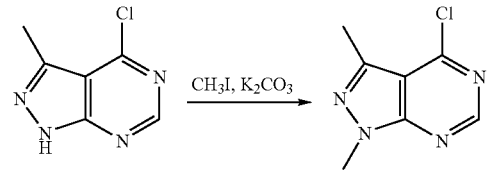

To a mixture of 4-chloro-3-methyl-1H-pyrazolo[3,4-d]pyrimidine (150.4 mg, 0.89 mmol, Example 3) and potassium carbonate (187 mg, 1.35 mmol) in dimethylformamide (6 mL) was added iodomethane (225 mg, 1.59 mmol, Aldrich). The reaction mixture was stirred at room temperature for 2 hours before it was diluted with ethyl acetate, washed with water, brine, dried and concentrated. The crude product was purified by flash chromatography (silica gel, hexanes-ethyl acetate, 90/10 to 60/40) to give 4-chloro-1,3-dimethyl-1H-pyrazolo[3,4-d]pyrimidine as a white solid. (Yield 162.3 mg).

HRMS (ES$^+$) m/z Calcd for $C_7H_7ClN_4$+H [(M+H)$^+$]: 183.0431. Found: 183.0432.

EXAMPLE 5

3-Bromomethyl-4-chloro-1-methyl-1H-pyrazolo[3,4-d]pyrimidine

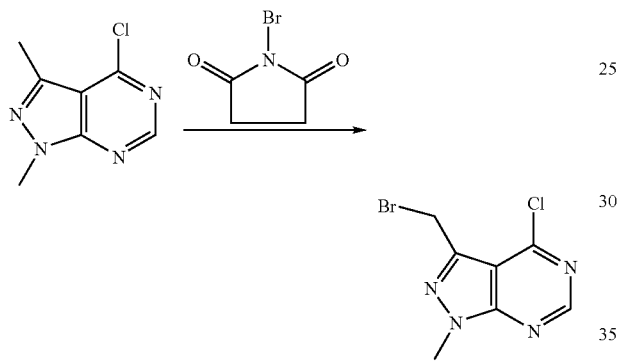

To a solution of 4-chloro-1,3-dimethyl-1H-pyrazolo[3,4-d]pyrimidine (752 mg, 4.12 mmol, Example 4) in carbon tetrachloride (45 mL) were added N-bromosuccinimide (964.4 mg, 5.36 mmol, Aldrich) and AIBN (209.6 mg, 1.25 mmol, Aldrich). The mixture was heated at reflux for 7 hours. The resulting reaction mixture was concentrated under reduced pressure and the residue was purified by flash chromatography (silica gel, hexanes-ethyl acetate, 95/5 to 70/30) to give 3-bromomethyl-4-chloro-1-methyl-1H-pyrazolo[3,4-d]pyrimidine as a white solid. (Yield 941.3 mg).

HRMS (ES$^+$) m/z Calcd for $C_7H_6BrClN_4$+H [(M+H)$^+$]: 260.9537. Found: 260.9537.

EXAMPLE 6

3-(3-Benzyloxy-phenoxymethyl)-4-chloro-1-methyl-1H-pyrazolo[3,4-d]pyrimidine

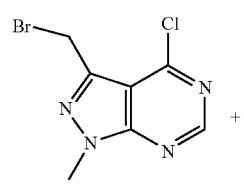 +

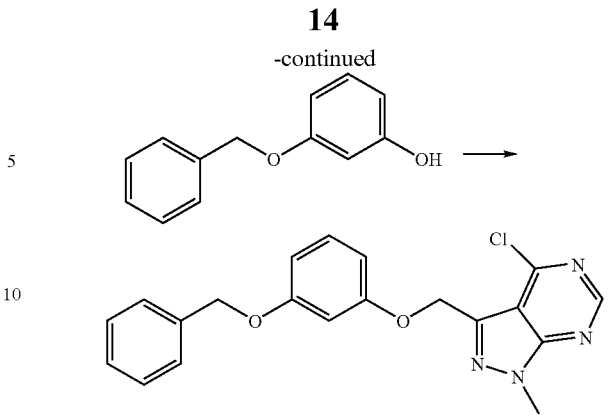

A mixture of 3-bromomethyl-4-chloro-1-methyl-1H-pyrazolo[3,4-d]pyrimidine (90.2 mg, 0.28 mmol, Example 5), 3-benzyloxy-phenol (75.2 mg, 0.36 mmol, TCI) and potassium carbonate (59.6 mg, 0.43 mmol) in dimethylformamide was stirred at room temperature overnight. The resulting mixture was concentrated under reduced pressure and the residue was dissolved in ethyl acetate, washed with water and brine, and dried and concentrated. The crude product was either used directly in the next step (described in Example 7) or purified by flash chromatography (silica gel, hexanes-ethyl acetate, 90/10 to 60/40) to give pure 3-(3-benzyloxy-phenoxymethyl)-4-chloro-1-methyl-1H-pyrazolo[3,4-d]pyrimidine. (Yield 33 mg).

HRMS (ES$^+$) m/z Calcd for $C_{20}H_{17}ClN_4O_2$+H [(M+H)$^+$]: 381.1115. Found: 381.1113.

EXAMPLE 7

3-(3-Benzyloxy-phenoxymethyl)-1-methyl-1H-pyrazolo[3,4-d]pyrimidin-4-ylamine

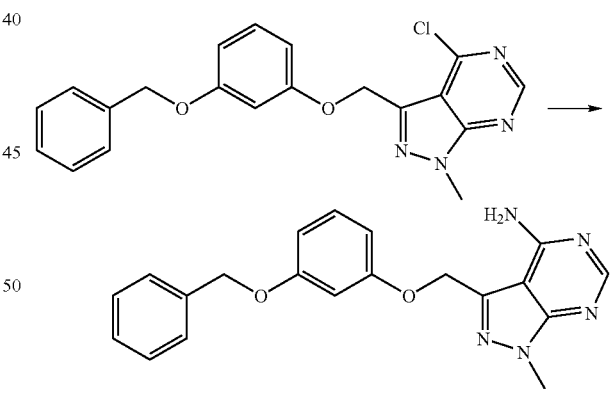

Ammonia gas was bubbled through a suspension of 3-(3-benzyloxy-phenoxymethyl)-4-chloro-1-methyl-1H-pyrazolo[3,4-d]pyrimidine (20 mg, Example 6) in 2-propanol (11 mL) for 15 minutes. The mixture was then heated at 130° C. for 1 hour under microwave condition. Solvent was removed under reduced pressure and the residue was purified by flash chromatography (silica gel, dichloromethane-methanol, 99/1 to 95/5) to give 3-(3-benzyloxy-phenoxymethyl)-1-methyl-1H-pyrazolo[3,4-d]pyrimidin-4-ylamine as a white solid. (Yield 5 mg).

HRMS (ES$^+$) m/z Calcd for $C_{20}H_{19}N_5O_2$+H [(M+H)$^+$]: 362.1611. Found: 362.1612.

EXAMPLE 8

3-Chloro-N-[3-(4-chloro-1-methyl-1H-pyrazolo[3,4-d]pyrimidin-3-ylmethoxy)-4-methyl-phenyl]-4-(2-hydroxy-ethylamino)-benzamide

Step 1

A solution of 3-chloro-4-fluorobenzoyl chloride (21.23 g, 110 mmol, Avocado) in tetrahydrofuran (50 mL) was added to a solution of 5-amino-o-cresol (6.16 g, 50 mmol, Aldrich), triethylamine (17.5 mL, 125 mmol, Aldrich) and tetrahydrofuran (50 mL) dropwise with magnetic stirring and cooling in an ice-water bath. When the addition was complete, the mixture was allowed to warm to room temperature and stirred for 16 hours. The mixture was then diluted with water (125 mL) and saturated aqueous sodium bicarbonate solution (125 mL). After stirring for another 30 minutes, precipitate was collected to give crude 3-chloro-4-fluoro-benzoic acid 5-(3-chloro-4-fluoro-benzoylamino)-2-methyl-phenyl ester as an off-white powder. (Yield 21.83 g).

3-Chloro-4-fluoro-benzoic acid 5-(3-chloro-4-fluoro-benzoylamino)-2-methyl-phenyl ester (3.93 g, 9 mmol, from above) was dissolved in a mixture of tetrahydrofuran (25 mL), methanol (50 mL) and aqueous 1N sodium hydroxide (9 mL, 9 mmol). The mixture was stirred at room temperature for 18 hours. The mixture was then concentrated under reduced pressure to remove most of the organic solvent. The resulting suspension was then diluted with water (45 mL) and saturated aqueous sodium bicarbonate solution (5 mL). After standing for 30 minutes, precipitate was collected, washed with water and dried to give crude 3-chloro-4-fluoro-N-(3-hydroxy-4-methyl-phenyl)-benzamide as a white powder. (Yield 2.59 g).

Step 2

A solution of 3-chloro-4-fluoro-N-(3-hydroxy-4-methyl-phenyl)-benzamide (1.0 g, 3.58 mmol, from above) in dimethylsulfoxide (5.0 mL) was treated with ethanolamine (10.0 mL) (Aldrich) and heated at 140° C. for 50 minutes in a microwave reactor. The reaction mixture was then partitioned between ethyl acetate and water. The aqueous phase was acidified with 2N hydrochloric acid. The precipitate was filtered, washed with water and dried. The aqueous phase was extracted with ethyl acetate (2×). The combined organic phase was washed with water and brine, dried (magnesium sulfate) and concentrated. The two solid samples were combined and dried to give 3-chloro-4-(2-hydroxy-ethylamino)-N-(3-hydroxy-4-methyl-phenyl)-benzamide. (Yield 1.13 g).

Step 3

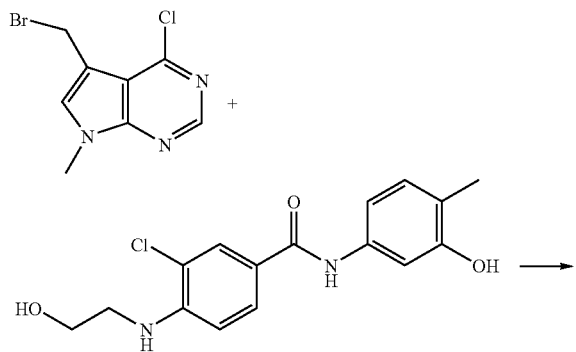

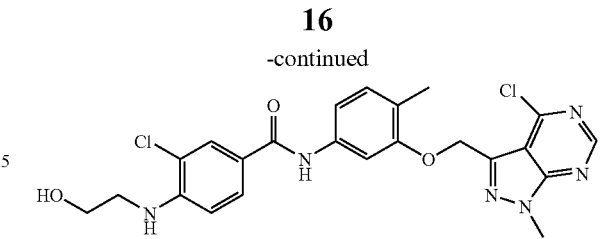

A mixture of 3-chloro-4-(2-hydroxyethylamino)-N-(3-hydroxy-4-methyl-phenyl)-benzamide (34.2 mg, 0.11 mmol) and potassium carbonate (17.3 mg, 0.123 mmol) was stirred at room temperature for 30 minutes before 3-bromomethyl-4-chloro-1-methyl-1H-pyrazolo[3,4-d]pyrimidine (25.4 mg, 0.097 mmole, Example 5) was added. The reaction was stirred at room temperature overnight and then concentrated under reduced pressure to remove dimethylformamide. The residue was dissolved in ethyl acetate, washed with water, dried and concentrated. The crude product was either used directly in the next step (described in Example 9) or purified by flash chromatography (silica gel, hexanes-ethyl acetate, 90/10 to 60/40) to give pure 3-chloro-N-[3-(4-chloro-1-methyl-1H-pyrazolo[3,4-d]pyrimidin-3-ylmethoxy)-4-methyl-phenyl]-4-(2-hydroxy-ethylamino)-benzamide as a white solid. (Yield 22 mg).

HRMS (ES⁺) m/z Calcd for $C_{23}H_{22}Cl_2N_6O_3$+H [(M+H)⁺]: 501.1197. Found: 503.1203.

EXAMPLE 9

N-[3-(4-Amino-1-methyl-1H-pyrazolo[3,4-d]pyrimidin-3-ylmethoxy)-4-methyl-phenyl]-3-chloro-4-(2-hydroxy-ethylamino)-benzamide

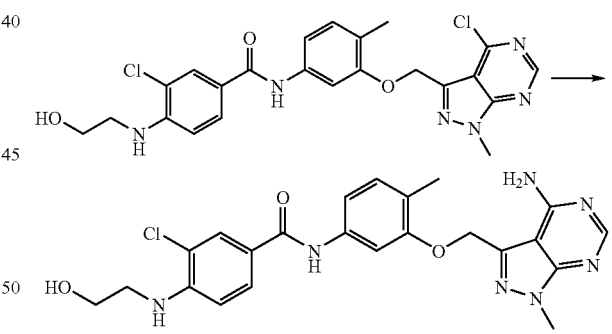

Ammonia gas was bubbled through a suspension of 3-chloro-N-[3-(4-chloro-1-methyl-1H-pyrazolo[3,4-d]pyrimidin-3-ylmethoxy)-4-methyl-phenyl]-4-(2-hydroxy-ethylamino)-benzamide (20.9 mg, Example 8) in 2-propanol (10 mL) for 15 minutes. The mixture was then heated at 130° C. for 1 hour under microwave conditions before the solvent was removed under reduced pressure. The residue was purified by flash chromatography (silica gel, dichloromethane-methanol, 99/1 to 95/5) to give N-[3-(4-amino-1-methyl-1H-pyrazolo[3,4-d]pyrimidin-3-ylmethoxy)-4-methyl-phenyl]-3-chloro-4-(2-hydroxy-ethylamino)-benzamide. (Yield 7.9 mg).

HRMS (ES⁺) m/z Calcd for $C_{23}H_{24}ClN_7O_3$+H [(M+H)⁺]: 482.1702. Found: 482.1702.

EXAMPLE 10

3-Chloro-N-[3-(4-chloro-1-methyl-1H-pyrazolo[3,4-d]pyrimidin-3-ylmethoxy)-4-methyl-phenyl]-benzamide Step 1

A solution of 3-chlorobenzoyl chloride (32.81 g, 187.5 mmol, Aldrich) in tetrahydrofuran (50 mL) was added to a solution of 5-amino-o-cresol (9.24 g, 75 mmol, Aldrich), triethylamine (31.43 mL, 225 mmol, Aldrich) and tetrahydrofuran (150 mL) dropwise with magnetic stirring and cooling in an ice-water bath. When the addition was complete, the mixture was allowed to warm to room temperature and stirred for 16 hours. The mixture was then diluted with water (200 mL) and saturated aqueous sodium bicarbonate solution (200 mL). After stirring for another 30 minutes, precipitate was collected to give crude 3-chloro-benzoic acid 5-(3-chloro-benzoylamino)-2-methyl-phenyl ester as an off-white powder. (Yield 31.74 g). Crude 3-chloro-benzoic acid 5-(3-chloro-benzoylamino)-2-methyl-phenyl ester (11.42 g, 28.5 mmol) was dissolved in a mixture of tetrahydrofuran (70 mL), methanol (140 mL) and aqueous 1N sodium hydroxide (28.5 mL, 28.5 mmol). The mixture was stirred at room temperature for 18 hours and then concentrated under reduced pressure to remove most of the organic solvent. The resulting suspension was diluted with water (90 mL) and saturated aqueous sodium bicarbonate solution (10 mL). After standing for 30 minutes, precipitate was collected, washed with water and dried to give 3-chloro-N-(3-hydroxy-4-methyl-phenyl)-benzamide as an off white powder. (Yield 6.06 g).

Step 2

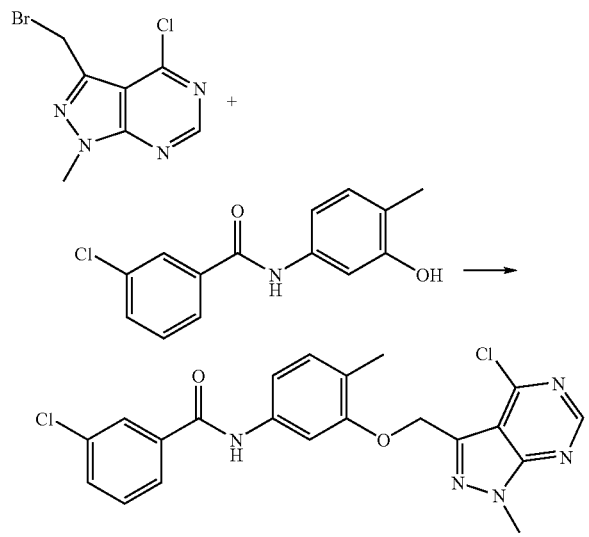

A mixture of 3-chloro-N-(3-hydroxy-4-methyl-phenyl)-benzamide (100 mg, 0.38 mmol, 36721-253A) and potassium carbonate (63.1 mg, 0.45 mmol) was stirred at room temp for 30 minutes before 3-bromomethyl-4-chloro-1-methyl-1H-pyrazolo[3,4-d]pyrimidine (90.9 mg, 0.28 mmol, Example 5) was added. The reaction was stirred at room temperature overnight and then concentrated under reduced pressure to remove dimethylformamide. The residue was dissolved in ethyl acetate, washed with water, dried and concentrated. The crude product was either used directly in the next step (described in Example 11) or purified by flash chromatography (silica gel, hexanes-ethyl acetate, 90/10 to 60/40) to give pure 3-chloro-N-[3-(4-chloro-1-methyl-1H-pyrazolo[3,4-d]pyrimidin-3-ylmethoxy)-4-methyl-phenyl]-benzamide as a white solid. (Yield 33.3 mg).

EXAMPLE 11

N-[3-(4-Amino-1-methyl-1H-pyrazolo[3,4-d]pyrimidin-3-ylmethoxy)-4-methyl-phenyl]-3-chloro-benzamide

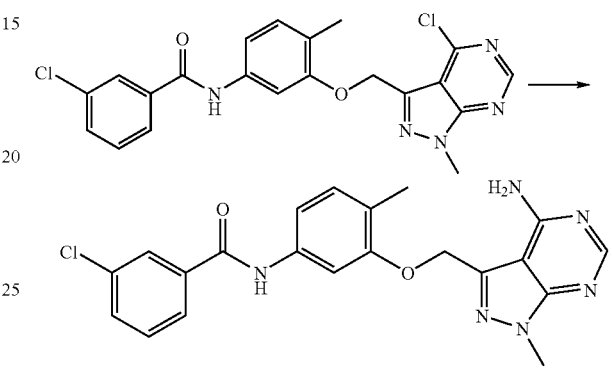

Ammonia gas was bubbled through a suspension of 3-chloro-N-[3-(4-chloro-1-methyl-1H-pyrazolo[3,4-d]pyrimidin-3-ylmethoxy)-4-methyl-phenyl]-benzamide (56.7 mg, Example 10) in 2-propanol (15 mL) for 15 minutes. The mixture was then heated at 130° C. for 1 hour under microwave conditions before the solvent was removed under reduced pressure. The residue was purified by flash chromatography (silica gel, dichloromethane-methanol, 99/1 to 95/5) to give N-[3-(4-amino-1-methyl-1H-pyrazolo[3,4-d]pyrimidin-3-ylmethoxy)-4-methyl-phenyl]-3-chloro-benzamide. (Yield 46.7 mg).

HRMS (ES$^+$) m/z Calcd for $C_{21}H_{19}ClN_6O_2$+H [(M+H)$^+$]: 423.1331. Found: 423.1331.

EXAMPLE 12

4-Chloro-1-methyl-3-[2-methyl-5-(3-methyl-[1,2,4]oxadiazol-5-yl)-phenoxymethyl]-1H-pyrazolo[3,4-d]pyrimidine Step 1

A mixture of 3-hydroxy-4-methylbenzoic acid (25.0 g, 164 mmol, Aldrich) and concentrated sulfuric acid (3 mL) in absolute ethanol (165 mL) was heated at reflux for 20 hours. After cooling, solid sodium bicarbonate (7 g) was added to neutralize the acid. The mixture was then partitioned between diethyl ether (2×300 mL) and water (2×300 mL). The organic layers were washed with brine (300 mL), combined, dried (MgSO$_4$), filtered, and concentrated. The residue was recrystallized from hexanes to give 3-hydroxy-4-methyl-benzoic acid ethyl ester in two crops as white crystals. (Yield 28.90 g, 97.8%).

Step 2

Sodium hydride (60% in oil, 4.80 g, 120 mmol, Aldrich) was washed with pentane (2×50 mL). Pentane was removed by pipetting. The resulting solid was suspended in anhydrous dimethylformamide (30 mL) and cooled in an ice-water bath. A solution of 3-hydroxy-4-methyl-benzoic acid ethyl ester (14.42 g, 80 mmol) in dimethylformamide (30 mL) was added dropwise over 30 minutes. After stirring for another 30 minutes chloromethyl methyl ether (8.2 mL, 108 mmol, Aldrich) was added dropwise over 10 minutes. After stirring at room temperature for another 2 hours, the reaction mixture was partitioned between water (3×250 mL) and diethyl ether (2×250 mL). Organic layers were washed with brine (250 mL), then combined, dried (MgSO$_4$), filtered and concentrated to give a colorless oil. This was filtered through silica gel (Biotage 40L, dichloromethane-hexanes, v/v 2:3, then dichloromethane) to give crude 3-methoxymethoxy-4-methyl-benzoic acid ethyl ester as a colorless oil (containing trace amounts of lower Rf material). (Yield 18.01 g, 100%).

Step 3

3-Methoxymethoxy-4-methyl-benzoic acid ethyl ester (4.5 g, 20 mmol) was dissolved in a mixture of ethanol (50 mL), water (20 mL) and 1 N aqueous sodium hydroxide solution (30 mL) and stirred at room temperature for 18 hours. The mixture was concentrated under reduced pressure to remove most of the ethanol. The resulting aqueous solution was acidified by adding acetic acid (2.5 g, 41.6 mmol). White precipitate was formed. After standing for another 30 minutes, the precipitate was collected by filtration, washed with water and dried to give crude 3-methoxymethoxy-4-methyl-benzoic acid as a white powder. (Yield 3.82 g, 97.0%).

Step 4

A mixture of 3-methoxymethoxy-4-methyl-benzoic acid (1.96 g, 10 mmol), 1-(3-dimethyl-aminopropyl-3-ethylcarbodiimide (1.92 g, 10 mmol, Aldrich), and 1-hydroxybenzotriazole hydrate (1.5 g, 10 mmol, Aldrich) was stirred at room temperature for 30 minutes. Acetamide oxime (0.74 g, 10 mmol) (GFS Chemicals) was added and the mixture heated at 140° C. with magnetic stirring for 2 hours. After cooling, the mixture was partitioned between ethyl acetate (2×100 mL) and saturated aqueous sodium bicarbonate solution (100 mL). Ethyl acetate solutions were combined and concentrated to give crude 5-(3-methoxymethoxy-4-methyl-phenyl)-3-methyl-[1,2,4]oxadiazole. (Yield 1.23 g, 52.5%).

Step 5

To a solution of 5-(3-methoxymethoxy-4-methyl-phenyl)-3-methyl-[1,2,4]oxadiazole (1.23 g, 5.25 mmol) in tetrahydrofuran/isopropanol (1:1, 30 mL) was added 13.1 mL of 4M HCl in dioxane. The reaction mixture was stirred at room temperature for 18 hours. The solution was concentrated. The residue was diluted with ethyl acetate, washed with water and brine, dried (magnesium sulfate) and concentrated. The residue was recrystallized from ethyl acetate/hexane to afford 2-methyl-5-(3-methyl-[1,2,4]oxadiazol-5-yl)-phenol. (Yield 0.88 g, 88%).

Step 6

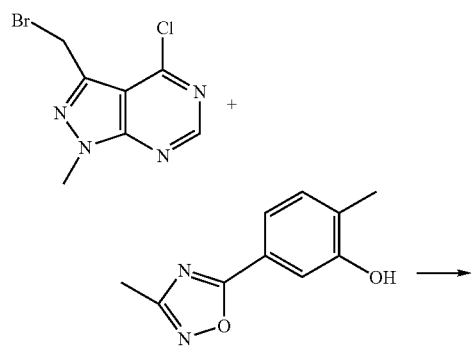

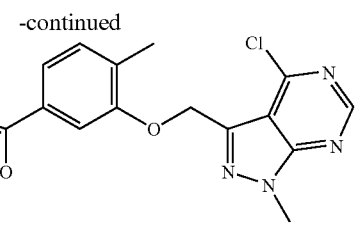

A mixture of 2-methyl-5-(3-methyl-[1,2,4]oxadiazol-5-yl)-phenol (72.0 mg, 0.0.379 mmol) and potassium carbonate (64.2 mg, 0.455 mmole) in dimethylformamide was stirred at room temperature for 30 minutes before 3-bromomethyl-4-chloro-1-methyl-1H-pyrazolo[3,4-d]pyrimidine (89.8 mg, 0.280 mmol, Example 5) was added. The reaction was stirred at room temperature overnight and then concentrated under reduced pressure to remove dimethylformamide. The residue was dissolved in ethyl acetate, washed with water, dried and concentrated. The crude product was purified by flash chromatography (silica gel, hexanes-ethyl acetate, 90/10 to 60/40) to give pure 4-chloro-1-methyl-3-[2-methyl-5-(3-methyl-[1,2,4]oxadiazol-5-yl)-phenoxymethyl]-1H-pyrazolo[3,4-d]pyrimidine as a white solid. (Yield 41.0 mg).

EXAMPLE 13

4-Chloro-1-methyl-3-[2-methyl-5-(3-methyl-[1,2,4]oxadiazol-5-yl)-phenoxymethyl]-1H-pyrazolo[3,4-d]pyrimidine

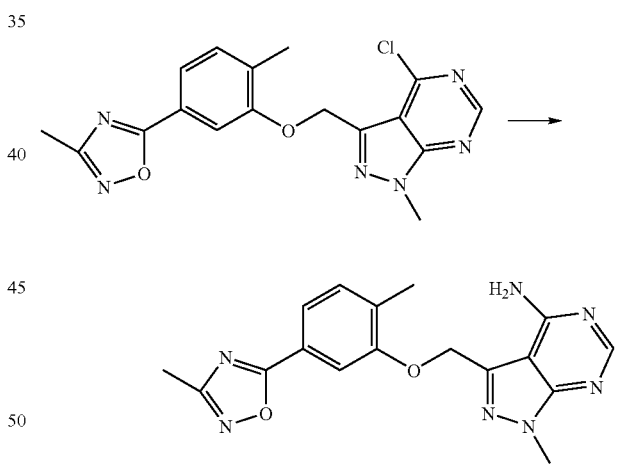

Ammonia gas was bubbled through a suspension of 4-chloro-1-methyl-3-[2-methyl-5-(3-methyl-[1,2,4]oxadiazol-5-yl)-phenoxymethyl]-1H-pyrazolo[3,4-d]pyrimidine (40.0 mg, Example 12) in 2-propanol (15 mL) for 15 minutes. The mixture was then heated at 130° C. for 1 hour under microwave conditions before solvent was removed under reduced pressure. The residue was purified by flash chromatography silica gel, dichloromethane-methanol, 99/1 to 95/5) to give 4- Amino-1-1-methyl-3- [2-methyl-5-(3-methyl-[1,2,4]oxadiazol-5-yl)-phenoxymethyl]-1H-pyrazolo[3,4-d]pyrimidine. (Yield 21.8 mg).

HRMS (ES$^+$) m/z Calcd for $C_{17}H_{17}N_7O_2$+H [(M+H)$^+$]: 352.1516. Found: 352.1517.

EXAMPLE 14

3-(5-Benzyloxy-2-methyl-phenoxymethyl)-4-chloro-1-methyl-1H-pyrazolo[3,4-d]pyrimidine Step 1

To a solution of 4-benzyloxy-2-hydroxybenzaldehyde (2.28 g, 10.0 mmol, prepared by the method of Example 18 below) and sodium cyanoborohydride (2.0 g, 15.9 mmol) in tetrahydrofuran (60 mL) was added methyl orange as an indicator, giving the solution a yellow color; 1N aqueous HCl solution (15 mL) was added slowly, keeping the solution orange. The mixture was stirred overnight at room temperature. Water was added, and the mixture was extracted with ethyl acetate three times. The combined organic phase was washed with water and brine, dried (MgSO$_4$) and concentrated. The residue was purified by flash chromatography eluting with 0-40% ethyl acetate in hexanes to give 5-benzyloxy-2-methyl-phenol. (Yield 0.64 g).

Step 2

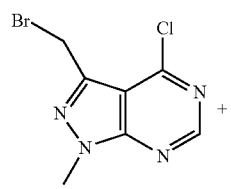

+

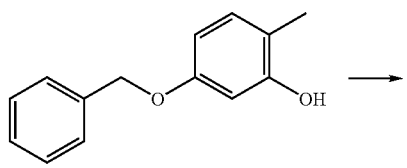

→

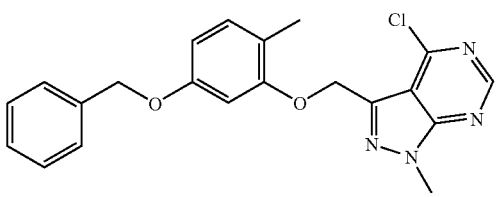

A mixture of 5-benzyloxy-2-methyl-phenol (83.4 mg, 0.389 mmol, 37009-93A) and potassium carbonate (61.8 mg, 0.438 mmole) was stirred at room temperature for 30 minutes before 3-bromomethyl-4-chloro-1-methyl-1H-pyrazolo[3,4-d]pyrimidine (89.8 mg, 0.344 mmole, Example 5) was added. The reaction was stirred at room temperature overnight and then concentrated under reduced pressure to remove dimethylformamide. The residue was dissolved in ethyl acetate, washed with water, dried and concentrated. The crude product was either used directly in the next step or purified by flash chromatography (silica gel, hexanes-ethyl acetate, 90/10 to 60/40) to give pure 3-(5-benzyloxy-2-methyl-phenoxymethyl)-4-chloro-1-methyl-1H-pyrazolo[3,4-d]pyrimidine as a white solid. (Yield 48.0 mg).

HRMS (ES$^+$) m/z Calcd for C$_{21}$H$_{19}$ClN$_4$O$_2$+H [(M+H)$^+$]: 395.1270. Found: 395.1270.

EXAMPLE 15

3-(5-Benzyloxy-2-methyl-phenoxymethyl)-1-methyl-1H-pyrazolo[3,4-d]pyrimidin-4-ylamine

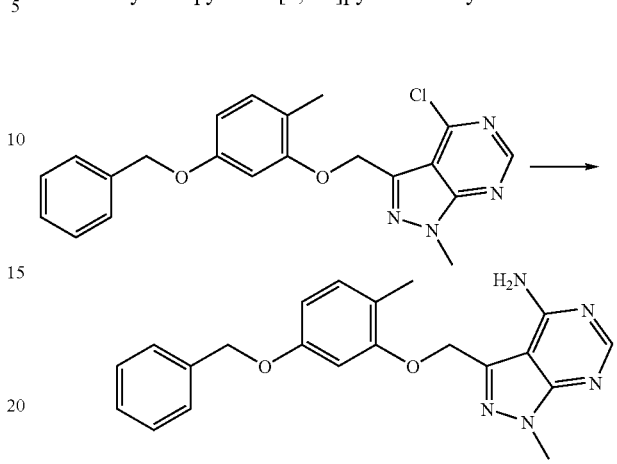

Ammonia gas was bubbled through a suspension of 3-(5-benzyloxy-2-methyl-phenoxymethyl)-4-chloro-1-methyl-1H-pyrazolo[3,4-d]pyrimidine (46.6 mg, Example 14) in 2-propanol (15 mL) for 15 minutes. The mixture was then heated at 130° C. for 1 hour under microwave conditions before the solvent was removed under reduced pressure. The residue was purified by flash chromatography (silica gel, dichloromethane-methanol, 99/1 to 95/5) to give 3-(5-benzyloxy-2-methyl-phenoxymethyl)-1-methyl-1H-pyrazolo[3,4-d]pyrimidin-4-ylamine. (Yield 34.5 mg).

HRMS (ES$^+$) m/z Calcd for C$_{21}$H$_{21}$N$_5$O$_2$+H [(M+H)$^+$]: 376.1768. Found: 376.1768.

EXAMPLE 16

3-(4-Chloro-1-methyl-1H-pyrazolo[3,4-d]pyrimidin-3-ylmethoxy)-N-(4-chloro-phenyl)-4-methyl-benzamide Step 1

A suspension of 3-hydroxy-4-methylbenzoic acid (10.73 g, 70.5 mmol, Lancaster) in acetic anhydride (25 mL, 265 mmol, Aldrich) was heated at reflux for 5 hours. After cooling to room temperature, the mixture was poured into an ice-water mixture (600 mL) and stirred overnight. Solid clumps were broken up and collected by filtration. The residue was washed with water and dried in a vacuum oven to give 3-acetoxy-4-methyl-benzoic acid as a tan solid. (Yield 11.82 g). 3-Acetoxy-4-methyl-benzoic acid (1.94 g, 10 mmol) was suspended in thionyl chloride (3 mL, 40 mmol, Aldrich) and N,N-dimethyl-formamide (3 drops) and heated at reflux for 2 hours. After cooling to room temperature, the mixture was diluted with toluene (30 mL) and concentrated under reduced pressure. The resulting oil was dissolved in dichloromethane (30 mL) and added dropwise to a solution of 4-chloroaniline (1.34 g, 10.5 mmol, Aldrich) and N,N-diisopropylethylamine (1.6 g, 12.5 mmol) in dichloromethane (50 mL). After stirring for another 2 hours, the mixture was diluted with water (50 mL) and stirred for another 30 minutes. The layers were separated. The organic layer was washed with water (50 mL). Aqueous layers were back washed with dichloromethane (50 mL). Organic layers were then combined and concentrated. The residue was dissolved in mixture of tetrahydrofuran (25 mL), methanol (25 mL) and 1 N aqueous sodium hydroxide (10 mL, 10 mmol). After stirring for 16 hours, the mixture was diluted with water (100 mL) and acetic acid (5 mL) and concentrated under reduced pressure to remove most of the organic solvent. Precipitate formed was collected by filtration and washed with water, and dried to give N-(4-chloro-phenyl)-3-hydroxy-4-methyl-benzamide as off-white crystals. (Yield 2.57 g).

Step 2

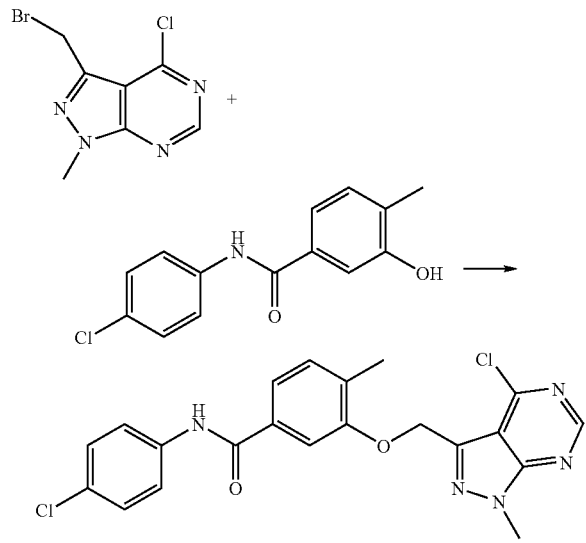

A mixture of N-(4-chloro-phenyl)-3-hydroxy-4-methyl-benzamide (127.4 mg, 0.487 mmol) and potassium carbonate (77.7 mg, 0.551 mmole) was stirred at room temperature for 30 minutes before 3-bromomethyl-4-chloro-1-methyl-1H-pyrazolo[3,4-d]pyrimidine (90.6 mg, 0.346 mmole, Example 5) was added. The reaction was stirred at room temperature overnight and then concentrated under reduced pressure to remove dimethylformamide. The residue was dissolved in ethyl acetate, washed with water, dried and concentrated. The crude product was either used directly in the next step (described in Example 17) or purified by flash chromatography (silica gel, hexanes-ethyl acetate, 90/10 to 60/40) to give pure 3-(4-chloro-1-methyl-1H-pyrazolo[3,4-d]pyrimidin-3-ylmethoxy)-N-(4-chloro-phenyl)-4-methyl-benzamide as a white solid. (Yield 25.0 mg).

HRMS (ES$^+$) m/z Calcd for $C_{21}H_{17}Cl_2N_5O_2$+H [(M+H)$^+$]: 442.0830. Found: 442.0832.

EXAMPLE 17

3-(4-Amino-1-methyl-1H-pyrazolo[3,4-d]pyrimidin-3-ylmethoxy)-N-(4-chloro-phenyl)-4-methyl-benzamide

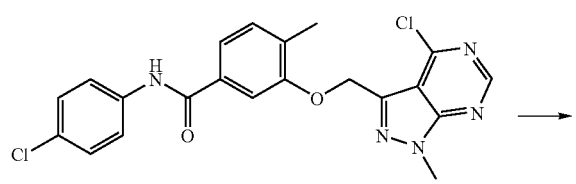

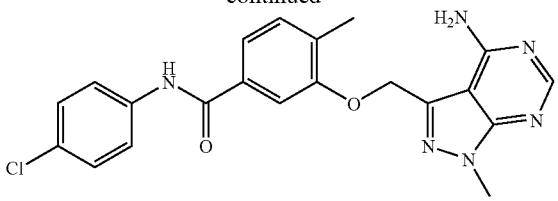

Ammonia gas was bubbled through a suspension of 3-(4-chloro-1-methyl-1H-pyrazolo[3,4-d]pyrimidin-3-ylmethoxy)-N-(4-chloro-phenyl)-4-methyl-benzamide (24.0 mg, Example 16) in 2-propanol (11 mL) for 15 minutes. The mixture was then heated at 130° C. for 1 hour under microwave conditions before solvent was removed under reduced pressure. The residue was purified by flash chromatography (silica gel, dichloromethane-methanol, 99/1 to 95/5) to give 3-(4-amino-1-methyl-1H-pyrazolo[3,4-d]pyrimidin-3-ylmethoxy)-N-(4-chloro-phenyl)-4-methyl-benzamide. (Yield 19.2 mg).

HRMS (ES$^+$) m/z Calcd for $C_{21}H_{19}ClN_6O_2$+H [(M+H)$^+$]: 423.1327. Found: 423.1331.

EXAMPLE 18

4-Chloro-3-[5-(4-chloro-benzyloxy)-2-methyl-phenoxymethyl]-1-methyl-1H-pyrazolo[3,4-d]pyrimidine Step 1

A mixture of 2,4-dihydroxybenzaldehyde (6.62 g, 48 mmol, Fluka), potassium fluoride (5.57 g, 96 mmol, Aldrich) and 4-chlorobenzyl chloride (13.50 g, 84 mmol, Aldrich) in acetonitrile (50 mL) was heated at 90° C. for 24 hours. After cooling, the mixture was partitioned between ether (2×100 mL) and water (2×100 mL). Organic layers were washed with brine (100 mL), combined, dried (MgSO$_4$), filtered and concentrated. The residue was purified by flash chromatography (Biotage 75S, hexanes, then hexanes-dichloromethane 1:1 as solvent) to give partial separation. Pure fractions of product were combined and concentrated and the residue crystallized from hexanes with traces of dichloromethane to give 4-(4-chloro-benzyloxy)-2-hydroxy-benzaldehyde as white crystals. (Yield 4.74 g). Mother liquor and impure fractions were combined and further purified by flash chromatography (Biotage 40L, same solvent as before) and pure fractions were combined and concentrated. The residue was re-crystallized to give second crop of 4-(4-chloro-benzyloxy)-2-hydroxy-benzaldehyde. (Yield 3.03 g).

Step 2

To a solution of 4-(4-chloro-benzyloxy)-2-hydroxybenzaldehyde (1.31 g, 5.0 mmol) and sodium cyanoborohydride (1.0 g, 15.9 mmol, Aldrich) in tetrahydrofuran (30 mL) was added methyl orange as an indicator, giving the solution a yellow color; 1N aqueous HCl solution (7.5 mL) was added slowly, keeping the solution orange. The mixture was then stirred overnight at room temperature. Water was added, and the mixture was extracted with ethyl acetate three times. The combined organic phase was washed with water and brine, dried (MgSO$_4$) and concentrated. The residue was purified by flash chromatography eluting with 0-40% ethyl acetate in hexanes to give 5-(4-chloro-benzyloxy)-2-methyl-phenol. (Yield 0.43 g).

Step 3

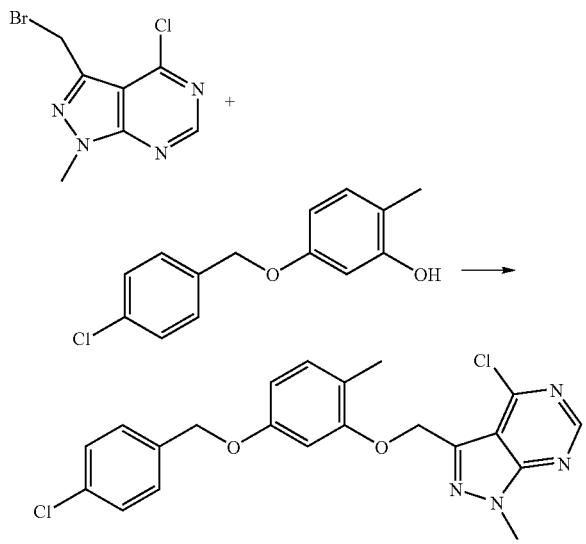

A mixture of 5-(4-chloro-benzyloxy)-2-methyl-phenol (95.6 mg, 0.384 mmol) and potassium carbonate (58.2 mg, 0.421 mmole) was stirred at room temperature for 30 minutes before 3-bromomethyl-4-chloro-1-methyl-1H-pyrazolo[3,4-d]pyrimidine (90.1 mg, 0.344 mmole, Example 5) was added. The reaction was stirred at room temperature overnight and then concentrated under reduced pressure to remove dimethylformamide. The residue was dissolved in ethyl acetate, washed with water, dried and concentrated. The crude product was purified by flash chromatography (silica gel, hexanes-ethyl acetate, 90/10 to 60/40) to give pure 4-chloro-3-[5-(4-chloro-benzyloxy)-2-methyl-phenoxymethyl]-1-methyl-1H-pyrazolo[3,4-d]pyrimidine as a white solid. (Yield 38.0 mg).

EXAMPLE 19

3-[5-(4-Chloro-benzyloxy)-2-methyl-phenoxymethyl]-1-methyl-1H-pyrazolo[3,4-d]pyrimidin-4-ylamine

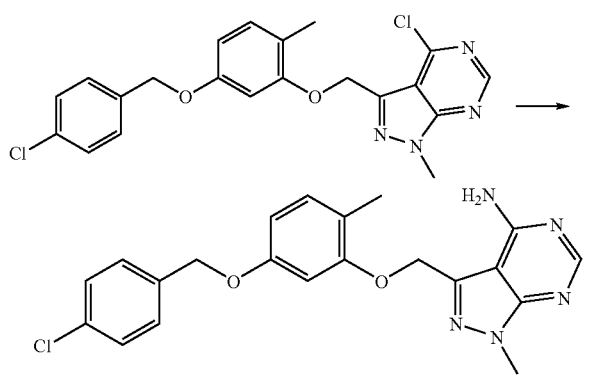

Ammonia gas was bubbled through a suspension of 4-chloro-3-[5-(4-chloro-benzyloxy)-2-methyl-phenoxymethyl]-1-methyl-1H-pyrazolo[3,4-d]pyrimidine (37.0 mg, Example 18) in 2-propanol (11 mL) for 15 minutes. The mixture was then heated at 130° C. for 1 hour under microwave conditions before the solvent was removed under reduced pressure. The residue was purified by flash chromatography (silica gel, dichloromethane-methanol, 99/1 to 95/5) to give 3-[5-(4-chloro-benzyloxy)-2-methyl-phenoxymethyl]-1-methyl-1H-pyrazolo[3,4-d]pyrimidin-4-ylamine. (Yield 25.0 mg).

HRMS (ES$^+$) m/z Calcd for $C_{21}H_{20}ClN_5O_2$+H [(M+H)$^+$]: 410.1379. Found: 410.1379.

EXAMPLE 20

4-Chloro-1-methyl-3-[2-methyl-5-(5-methyl-[1,3,4]oxadiazol-2-yl)-phenoxymethyl]-1H-pyrazolo[3,4-d]pyrimidine Step 1

A mixture of 3-hydroxy-4-methylbenzoic acid (25.42 g, 167 mmol, TCI US) and concentrated sulfuric acid (3 mL) in absolute ethanol (180 mL) was heated at reflux for 20 hours. After cooling, solid sodium bicarbonate (10 g) was added to neutralize the acid. The mixture was partitioned between diethyl ether (2×400 mL) and water (2×300 mL). The organic layers were washed with brine (300 mL), combined, dried (MgSO$_4$), filtered, and concentrated. The residue was recrystallized from hexanes to give 3-hydroxy-4-methyl-benzoic acid ethyl ester as white crystals in two crops. (Yield 29.14 g).

Step 2

A suspension of ethyl 3-hydroxy-4-methylbenzoate (3.60 g, 20 mmol) in anhydrous hydrazine (10 mL, 318 mmol) (Aldrich) was heated at reflux (150° C. bath temperature) for 3 hours. After cooling to room temperature, the mixture was concentrated under reduced pressure to give a dry solid. This was suspended in xylene (50 mL) and concentrated under reduced pressure. The resulting solid was suspended in triethyl ortho-acetate (35 mL, 191 mmol) (Aldrich) and heated at reflux (150° C. bath temperature) for 20 hours with removal of ethanol. After cooling, dichloromethane was added and the solid was collected by filtration to give 2-methyl-5-(5-methyl-[1,3,4]oxadiazol-2-yl)-phenol as an off-white crystalline material. (Yield 2.28 g).

Filtrate from the above was purified by flash chromatography (Biotage 40L, 10% then 40% ethyl acetate in dichloromethane as solvent) to give second crop of 2-methyl-5-(5-methyl-[1,3,4]oxadiazol-2-yl)-phenol as a white crystalline material. (Yield 0.99 g).

Step 3

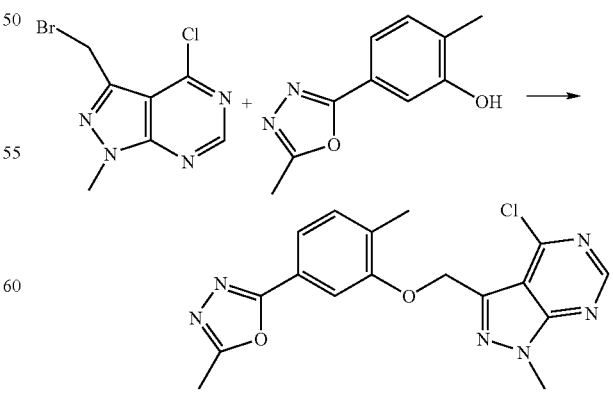

A mixture of 2-methyl-5-(5-methyl-[1,3,4]oxadiazol-2-yl)-phenol (73.3 mg, 0.385 mmol) and potassium carbonate (60.9 mg, 0.432 mmole) was stirred at room temperature for 30 minutes before 3-bromomethyl-4-chloro-1-methyl-1H-pyrazolo[3,4-d]pyrimidine (89.6 mg, 0.343 mmole, Example 5) was added. The reaction was stirred at room temperature overnight and then concentrated under reduced pressure to remove dimethylformamide. The residue was dissolved in ethyl acetate, washed with water, dried and concentrated. The crude product was either used directly in the next step or purified by flash chromatography (silica gel, hexanes-ethyl acetate, 90/10 to 60/40) to give pure 4-chloro-1-methyl-3-[2-methyl-5-(5-methyl-[1,3,4]oxadiazol-2-yl)-phenoxymethyl]-1H-pyrazolo[3,4-d]pyrimidine as a white solid. (Yield 34.9 mg).

EXAMPLE 21

1-Methyl-3-[2-methyl-5-(5-methyl-[1,3,4]oxadiazol-2-yl)-phenoxymethyl]-1H-pyrazolo[3,4-d]pyrimidin-4-ylamine

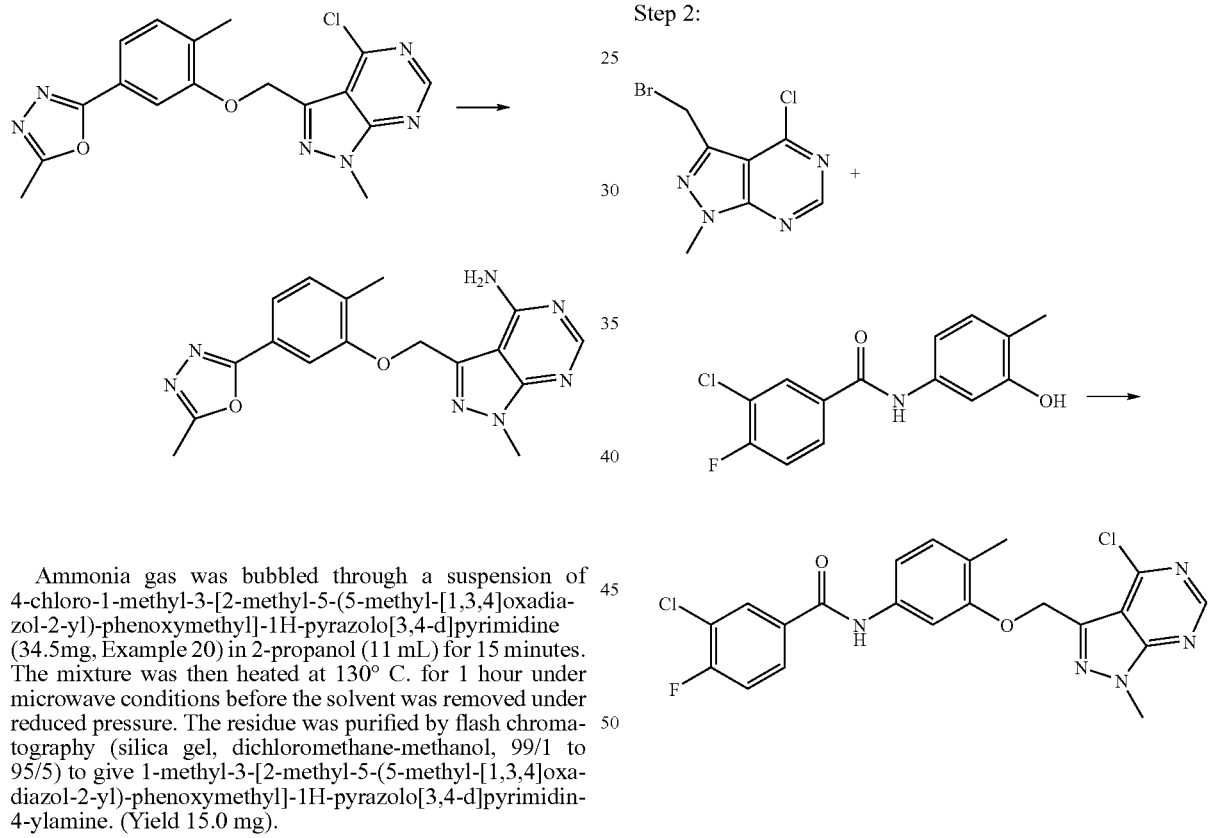

Ammonia gas was bubbled through a suspension of 4-chloro-1-methyl-3-[2-methyl-5-(5-methyl-[1,3,4]oxadiazol-2-yl)-phenoxymethyl]-1H-pyrazolo[3,4-d]pyrimidine (34.5 mg, Example 20) in 2-propanol (11 mL) for 15 minutes. The mixture was then heated at 130° C. for 1 hour under microwave conditions before the solvent was removed under reduced pressure. The residue was purified by flash chromatography (silica gel, dichloromethane-methanol, 99/1 to 95/5) to give 1-methyl-3-[2-methyl-5-(5-methyl-[1,3,4]oxadiazol-2-yl)-phenoxymethyl]-1H-pyrazolo[3,4-d]pyrimidin-4-ylamine. (Yield 15.0 mg).

EXAMPLE 22

N-(3-Chloro-4-fluoro-phenyl)-3-(4-chloro-1-methyl-1H-pyrazolo[3,4-d]pyrimidin-3-ylmethoxy)-4-methyl-benzamide Step 1:

A solution of 3-chloro-4-fluorobenzoyl chloride (21.23 g, 110 mmol, Avocado) in tetrahydrofuran (50 mL) was added to a solution of 5-amino-o-cresol (6.16 g, 50 mmol, Aldrich) and triethylamine (17.5 mL, 125 mmol, Aldrich) and tetrahydrofuran (50 mL) dropwise with magnetic stirring and cooling in an ice-water bath. When the addition was complete, the mixture was allowed to warm to room temperature and stirred for 16 hours. The mixture was then diluted with water (125 mL) and saturated aqueous sodium bicarbonate solution (125 mL). After stirring for another 30 minutes, the precipitate was collected to give crude 3-chloro-4-fluoro-benzoic acid 5-(3-chloro-4-fluoro-benzoylamino)-2-methyl-phenyl ester as an off-white powder. (Yield 21.83 g, 101%).

3-Chloro-4-fluoro-benzoic acid 5-(3-chloro-4-fluoro-benzoylamino)-2-methyl-phenyl ester (3.93 g, 9 mmol) was dissolved in a mixture of tetrahydrofuran (25 mL), methanol (50 mL) and aqueous 1N sodium hydroxide (9 mL, 9 mmol). The mixture was stirred at room temperature for 18 hours and then concentrated under reduced pressure to remove most of the organic solvent. The resulting suspension was diluted with water (45 mL) and saturated aqueous sodium bicarbonate solution (5 mL). After standing for 30 minutes, the precipitate was collected and washed with water and dried to give crude 3-chloro-4-fluoro-N-(3-hydroxy-4-methyl-phenyl)-benzamide as a white powder. (Yield 2.59 g, 103%).

Step 2:

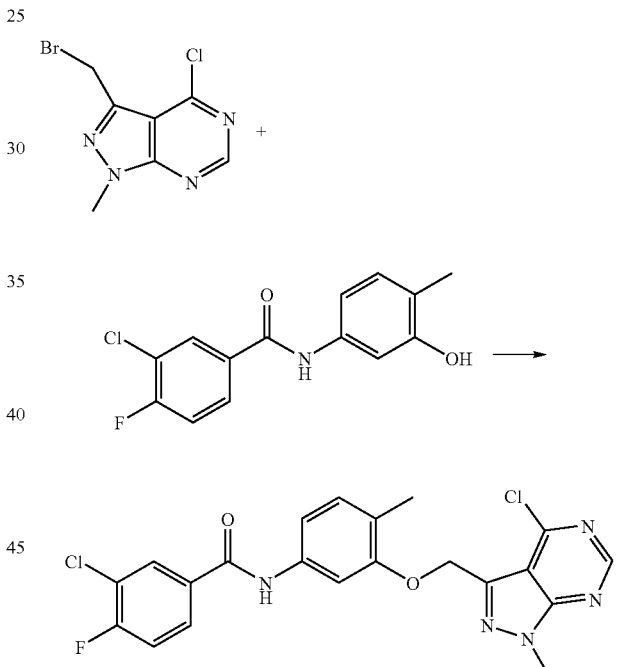

A mixture of 3-chloro-4-fluoro-N-(3-hydroxy-4-methyl-phenyl)-benzamide (105.9 mg, 0.379 mmol) and potassium carbonate (59.6 mg, 0.431 mmol) in dimethylformamide was stirred at room temperature for 30 minutes before 3-bromomethyl-4-chloro-1-methyl-1H-pyrazolo[3,4-d]pyrimidine (90.7 mg, 0.347 mmol, Example 5) was added. The reaction was stirred at room temperature overnight and then concentrated under reduced pressure to remove dimethylformamide. The residue was dissolved in ethyl acetate, washed with water, dried and concentrated. The crude product was either used directly for the next step or purified by flash chromatography (silica gel, hexanes-ethyl acetate, 90/10 to 50/50) to give pure 3-chloro-N-[3-(4-chloro-1-methyl-1H-pyrazolo[3, 4-d]pyrimidin-3-ylmethoxy)-4-methyl-phenyl]-4-fluoro-benzamide as a white solid. (Yield 35.5 mg).

EXAMPLE 23

3-(4-Amino-1-methyl-1H-pyrazolo[3,4-d]pyrimidin-3-ylmethoxy)-N-(3-chloro-4-fluoro-phenyl)-4-methyl-benzamide

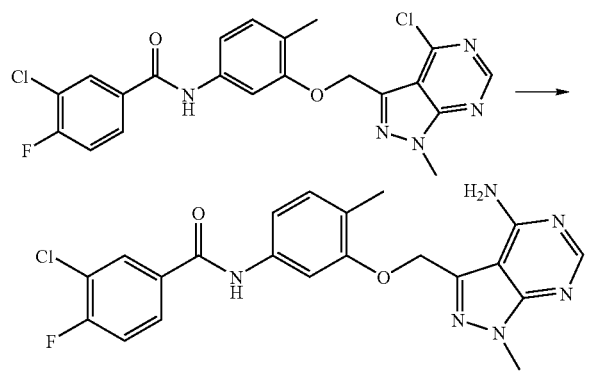

Ammonia gas was bubbled through a suspension of 3-chloro-N-[3-(4-chloro-1-methyl-1H-pyrazolo[3,4-d]pyrimidin-3-ylmethoxy)-4-methyl-phenyl]-4-fluoro-benzamide (34.5 mg, Example 22) in 2-propanol (11 mL) for 15 minutes. The mixture was then heated at 130° C. for 1 hour under microwave condition before solvent was removed under reduced pressure. The residue was purified by flash chromatography (silica gel, dichloromethane-methanol, 98/2 to 90/10) to give 3-(4-amino-1-methyl-1H-pyrazolo[3,4-d]pyrimidin-3-ylmethoxy)-4-methyl-phenyl]-3-chloro-4-fluoro-benzamide as a white solid. (Yield 25.6 mg).

HRMS (ES$^+$) m/z Calcd for $C_{21}H_{18}ClFN_6O_2$+H [(M+H)$^+$]: 441.1235. Found: 441.1237.

EXAMPLE 24

The antiproliferative activity of the compounds of the present invention is demonstrated below. These activities indicate that the compounds of the present invention are useful in treating cancer, in particular solid tumors such as breast tumor, lung tumor, colon tumor, prostate tumor, and melanoma.

Kinase Enzyme Inhibition Assay (IC$_{50}$)
c-Raf HTRF Assay With 6H-MEK as Substrate (Dose Response)
Assay Principle:

The assay utilizes 6H-MEK as the substrate. Upon c-Raf phosphorylation, phosphorylated 6H-MEK is detected with rabbit anti-phospho-MEK1/2, Eu-labeled anti-rabbit, and APC-labeled anti-6H antibodies.

Reagents and Instruments:
Enzyme: cloned human c-Raf with EE-tag; phosphorylated (co-expressed with v-src-FLAG in baculovirus Hi5 cells), 0.2 mg/mL (2.74 µM assuming a molecular weight of 73 kD) stored at −15° C.
Substrate: WT full-length 6H-MEK, 4.94 mg/mL (154.4 µM assuming a MW of 32 kD) stored at −15° C.
Antibodies: Rabbit (α-P-(Ser 217/221)-MEK-1/2 Ab (from Cell Signaling, Cat. #9121B, Lot 14); Eu-(α-rabbit IgG (from Wallac, Cat. #AD0083, Lot 318663, 710 ug/mL, 4.4 µM); (α-6H-SureLight-APC (from Martek, Cat. #AD0059H, Lot E012AB01, 3.03 µM).
Reader: Envision from PerkinElmer, HTRF reading mode with 412 mirror
Assay Plate: Matrix all-black polypropylene plates (Cat. #4344)
Others: Weidman 384 polypropylene plates (REMP) for compound plate.
Assay Procedure:
(1) Prepare Kinase Assay Buffer (KAB): 50 mM HEPES (HyClone) pH7, 10 mM MgCl$_2$, 1 mM DTT, 0.1 mM Na$_3$V$_2$O$_4$, and 0.3 mg/ml BSA.
(2) Prepare 6H-MEK (150 nM) in KAB. Add 12 µL/well to the assay plate.
(3) Prepare ATP (66 µM) in KAB.
(4) Dilute compounds to 2.4 mM and any positive controls to 480 µM in DMSO. Perform 10-point 3x dilution in DMSO. Withdraw 2.5 µL/well of DMSO solution and add to 27.5 µl/well ATP solution in (3).
(5) Mix, then add 6 µl/well of solution in (4) to the assay plate for a DMSO concentration of 2.1% during MEK phosphorylation.
(6) Prepare c-Raf (12 nM) in KAB.
(7) Add 6 µl/well of KAB in columns 1-2 and 6 µL/well of c-Raf in columns 3-24.
(8) Incubate at 37° C. for 30 min.
(9) Prepare rabbit (α-P-(Ser 217/221)-MEK-1/2 Ab (1:240 from stock) in AB1: 50 mM HEPES pH7, 0.2 mg/mL BSA, and 43 mM EDTA.
(10) To stop reaction, add 6 µL/well of solution from (9) to the assay plate and incubate at 37° C. for 30 min.
(11) Prepare Eu-(α-rabbit IgG (9 nM) and (α-6H-SureLight-APC (120 nM) in AB2: 50 mM HEPES pH7 and 0.2 mg/mL BSA.
(12) Add 6 µl/well of solution from (11) to the assay plate.
(13) For determining the spectrum cross talk factor, prepare 2 samples following steps (1) to (10). For the blank sample, add 6 µl/well of AB2. For the cross talk factor sample, add 6 µL/well of Eu-anti rabbit IgG (9 nM).
(14) Incubate at room temperature for 1.5 hours.
(15) Read HTRF signals at 615 nm and 665 nm on the Envision. Normalize HTRF signals after spectrum cross-talk correction.

Expression and Purification of c-Raf

N terminal EE-tagged c-Raf was expressed in High-5 cells. A five liter culture was co-transfected with virus for EE-c-Raf and FLAG-vSrc at a ratio of 1:2 and harvested after 48 hours. The cell pellet was lysed in TBS containing 5 mM EDTA, 50 mM KF, 20 mM Na pyrophosphate, 20 mM β-glycerolphosphate, 0.5 mM NaVO$_3$, 1% NP-40 (w/v) and Complete Protease Tablets. The lysate was centrifuged at 20,000×g for 1 hour. The supernatant was incubated with 8 mL of anti-EE tag-Protein G Sepharose for 2 hours at 4° C. The resin was then washed with 30 volumes of the above buffer. The c-Raf protein was eluted by incubation with the above buffer containing 100 mg/mL of EE peptide for 1 hour at 4° C. The protein was concentrated using an Amicon Stir Cell with an YM10 membrane. The concentrated protein was dialyzed against TBS containing 1 mM DTT and 30% Glycerol. Protein concentration was determined by the BioRad DC method.

Purification of 6H-MEK1 (62-393)

E. coli cells containing the plasmid for the expression of 6H-MEK1 (62-393) were grown in Rich Media and induced with 1 mM IPTG for 24 hours at 22° C. The cell pellet was resuspended in 50 mM potassium phosphate buffer, pH 8.0, 300 mM NaCl, 5 mM MgCl$_2$, 10 mM CHAPS, 2 mM TCEP, and Complete Protease Inhibitor Tablets. Cells were disrupted by sonication. The lysate was cleared by centrifugation at 13,000×g for 45 minutes. The supernatant was diluted 1:1 with 50 mM potassium phosphate buffer, pH 8.0, 10 mM imidazole, 4 mM TCEP, 300 mM NaCl, 10 mM CHAPS, 2 mM pyrrole-2-carboxylate, and 100 mM $ZnCl_2$, then incubated with TALON metal affinity resin for 1 hour at 4° C. The resin was washed with 10 volumes of 50 mM potassium phosphate buffer, pH 8.0, 5 mM imidazole, 2 mM TCEP, 300 mM NaCl, 10 mM CHAPS, 1 mM pyrrole-2-carboxylate, and 50 mM $ZnCl_2$. Proteins were eluted by incubation with 5 volumes of 20 mM HEPES, pH 8.0, 100 mM EDTA, 2 mM TCEP, 10% v/v glycerol for 1 hour at 4° C. The eluted material was concentrated using Amicon Ultra 15 devices with 10 Kd MW cutoff membranes. The sample was then subjected to size exclusion chromatography on a Superdex 200 26/60 column. The 6H-MEK1 Peak was pooled and concentrated as above. Protein was determined by the BioRad method.

b-Raf Wild-Type HTRF Assay With 6H-MEK as Substrate (Dose Response)

Assay Principle:

The assay utilizes 6H-MEK as the substrate. Upon b-Raf WT phosphorylation, phosphorylated 6H-MEK is detected with rabbit anti-phospho-MEK1/2, Eu-labeled anti-rabbit, and APC-labeled anti-6H antibodies.

Reagents and Instruments:

Enzyme: recombinant human b-Raf residues 416-end with N-terminal GST-tag from Upstate; (expressed by baculovirus in Sf21 insect cells), 0.26 mg/mL (3.87 µM assuming a molecular weight of 67.2 kD) Cat. #14-530M, Lot #25502AU, stored at −80° C.

Substrate: WT full-length 6H-MEK, 4.94 mg/mL (154.4 µM assuming a MW of 32 kD) stored at −15° C.

Antibodies: Rabbit (α-P-(Ser 217/221)-MEK-1/2 Ab (from Cell Signaling, Cat. #9121B, Lot 14); Eu-(α-rabbit IgG (from Wallac, Cat. #AD0083, Lot 318663, 710 ug/mL, 4.4 µM); (α-6H-SureLight-APC (from Martek, Cat. #AD0059H, Lot E012AB01, 3.03 µM).

Reader: Envision from PerkinElmer, HTRF reading mode with 412 mirror

Assay Plate: Matrix all-black polypropylene plates (Cat. #4344)

Others: Weidman 384 polypropylene plates (REMP) for compound plate.

Assay Procedure:
(1) Prepare Kinase Assay Buffer (KAB): 50 mM HEPES (HyClone) pH7, 10 mM $MgCl_2$, 1 mM DTT, 0.1 mM $Na_3V_2O_4$, and 0.3 mg/ml BSA.
(2) Prepare 6H-MEK (150 nM) in KAB. Add 12 µL/well to the assay plate.
(3) Prepare ATP (66 µM) in KAB.
(4) Dilute compounds to 2.4 mM and any positive controls to 480 µM in DMSO. Perform 10-point 3× dilution in DMSO. Withdraw 2.5 µL/well of DMSO solution and add to 27.5 µL/well ATP solution in (3).
(5) Mix, then add 6 µL/well of solution in (4) to the assay plate for a DMSO concentration of 2.1% during MEK phosphorylation.
(6) Prepare b-Raf WT (100 µM) in KAB.
(7) Add 6 µL/well of KAB in columns 1-2 and 6 µL/well of b-Raf WT in columns 3-24.
(8) Incubate at 37° C. for 30 min.
(9) Prepare rabbit (α-P-(Ser 217/221 )-MEK-1/2 Ab (1:200 from stock) in AB1: 50 mM HEPES pH7, 0.2 mg/ml BSA, and 43 mM EDTA.
(10) To stop reaction, add 6 µL/well of solution from (9) to the assay plate and incubate at 37° C. for 30 min.
(11) Prepare Eu-(α-rabbit IgG (9 nM) and (α-6H-SureLight-APC (180 nM) in AB2: 50 mM HEPES pH7 and 0.2 mg/mL BSA.
(12) Add 6 µL/well of solution from (11) to the assay plate.
(13) For determining the spectrum cross talk factor, prepare 2 samples following steps (1) to (10). For the blank sample, add 6 µL/well of AB2. For the cross talk factor sample, add 6 µL/well of Eu-anti rabbit IgG (9 nM).
(14) Incubate at room temperature for 1.5 hours.
(15) Read HTRF signals at 615 nm and 665 nm on the Envision. Normalize HTRF signals after spectrum cross-talk correction.

b-Raf V600E Mutant HTRF Assay With 6H-MEK as Substrate (Dose Response)

Assay Principle:

The assay utilizes 6H-MEK as the substrate. Upon b-Raf V600E phosphorylation, phosphorylated 6H-MEK is detected with rabbit anti-phospho-MEK1/2, Eu-labeled anti-rabbit, and APC-labeled anti-6H antibodies.

Reagents and Instruments:

Enzyme: recombinant human b-Raf residues 416-end containing a V600E mutation with N-terminal GST-tag from Upstate; (expressed by baculovirus in Sf21 insect cells), 0.26 mg/mL (7.49 µM assuming a molecular weight of 67.3 kD) Cat. #14-5M, Lot #25633AU, stored at −80° C.

Substrate: WT full-length 6H-MEK, 4.94 mg/mL (154.4 µM assuming a MW of 32 kD) stored at −15° C.

Antibodies: Rabbit (α-P-(Ser 217/221)-MEK-1/2 Ab (from Cell Signaling, Cat. #9121B, Lot 14); Eu-(α-rabbit IgG (from Wallac, Cat. #AD0083, Lot 318663, 710 ug/mL, 4.4 µM); (α-6H-SureLight-APC (from Martek, Cat. #AD0059H, Lot E012AB01, 3.03 µM).

Reader: Envision from PerkinElmer, HTRF reading mode with 412 mirror

Assay Plate: Matrix all-black polypropylene plates (Cat. #4344)

Others: Weidman 384 polypropylene plates (REMP) for compound plate.

Assay Procedure:
(1) Prepare Kinase Assay Buffer (KAB): 50 mM HEPES (HyClone) pH7, 10 mM $MgCl_2$, 1 mM DTT, 0.1 mM $Na_3V_2O_4$, and 0.3 mg/ml BSA.
(2) Prepare 6H-MEK (150 nM) in KAB. Add 12 µl/well to the assay plate.
(3) Prepare ATP (66 µM) in KAB.
(4) Dilute compounds to 2.4 mM and positive controls to 480 µM in DMSO. Perform 10-point 3× dilution in DMSO. Withdraw 2.5 µL/well of DMSO solution and add to 27.5 µL/well ATP solution in (3).
(5) Mix, then add 6 µL/well of solution in (4) to the assay plate for a DMSO concentration of 2.1% during MEK phosphorylation.
(6) Prepare b-Raf V600E (100 µM) in KAB.
(7) Add 6 µL/well of KAB in columns 1-2 and 6 µL/well of b-Raf V600E in columns 3-24.
(8) Incubate at 37° C. for 30 min.
(9) Prepare rabbit α-P-(Ser 217/221 )-MEK-1/2 Ab (1:200 from stock) in AB1: 50 mM HEPES pH7, 0.2 mg/mL BSA, and 43 mM EDTA.
(10) To stop reaction, add 6 µL/well of solution from (9) to the assay plate and incubate at 37° C. for 30 min.
(11) Prepare Eu-α-rabbit IgG (9 nM) and α-6H-SureLight-APC (180 nM) in AB2: 50 mM HEPES pH7 and 0.2 mg/mL BSA.
(12) Add 6 µL/well of solution from (11) to the assay plate.

(13) For determining the spectrum cross talk factor, prepare 2 samples following steps (1) to (10). For the blank sample, add 6 µL/well of AB2. For the cross talk factor sample, add 6 µL/well of Eu-anti rabbit IgG (9 nM).
(14) Incubate at room temperature for 1.5 hours.
(15) Read HTRF signals at 615 nm and 665 nm on the Envision. Normalize HTRF signals after spectrum cross-talk correction.

Assay Data

TABLE 1

| | Kinase enzyme inhibition assay (IC$_{50}$) | | |
|---|---|---|---|
| Example | cRaf IC$_{50}$ (µM) | bRaf wild-type IC$_{50}$ (µM) | bRaf(V600E) IC$_{50}$ (µM) |
| 9 | <10 | <10 | <10 |
| 17 | <10 | <10 | <10 |
| 23 | <10 | <10 | <10 |
| 13 | <10 | >10 | >10 |
| 11 | <10 | <10 | <10 |
| 15 | <10 | <10 | <10 |
| 7 | <10 | >10 | >10 |
| 19 | <10 | <10 | <10 |
| 21 | <10 | >10 | >10 |

What is claimed:
1. A compound according to Formula (I),

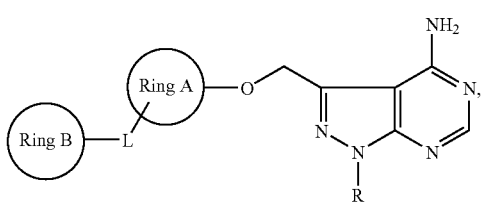

(I)

wherein
R is lower alkyl;
Ring A is selected from the group consisting of:
  heteroaryl;
  heteroaryl substituted by 1 to 5 substituents independently selected from the group consisting of: lower alkyl; halogen; hydroxyl; lower alkoxy; lower alkoxy substituted by hydroxyl or lower alkoxy; and cyano; phenyl; and
  phenyl substituted by 1 to 4 substituents independently selected from the group consisting of: lower alkyl; halogen; hydroxyl; lower alkoxy; lower alkoxy substituted by hydroxyl or lower alkoxy; and cyano;
Ring B is selected from the group consisting of:
  heteroaryl;
  heteroaryl substituted by 1 to 5 substituents selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —NR$^1$R$^2$;
  phenyl; and
  phenyl substituted by 1 to 5 substituents selected from the group consisting of: lower alkyl; fluorinated alkyl; aryl-substituted alkyl; hydroxyl; lower alkoxy; lower alkoxy substituted by hydroxyl or lower alkoxy; halogen; and —NR$^1$R$^2$;
R$^1$ and R$^2$ are each independently selected from the group consisting of hydrogen, lower alkyl, and lower alkyl substituted with hydroxyl or lower alkoxy, and R$^1$ and R$^2$, together with N, can form a 5- or 6-membered heterocyclic ring; and
L is selected from the group consisting of: a bond, —OCH$_2$—, —CH$_2$O—, —NHCO—, —CONH—, —O—, —OCH$_2$CH$_2$—, —CH$_2$OCH$_2$—, —CH$_2$CH$_2$O—, —CF═CH—, —CH═CF—, —NH—, —NHCH$_2$—, —CH$_2$NH—, —SCH$_2$—, —CH$_2$S—, —SOCH$_2$—, —CH$_2$SO—, —SO$_2$CH$_2$—, —CH$_2$SO$_2$—, —S—, —CH═CH—, and lower alkyl;
with the proviso that, when L is a bond, Ring B is an azole substituted by 1 to 4 substituents selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —NR$^1$R$^2$;
or a pharmaceutically-acceptable salt or ester of a compound according to Formula (I).

2. A compound according to claim 1 wherein Ring A is substituted by 1 substituent.

3. A compound according to claim 1 wherein Ring B is substituted by 1 or 2 substituents.

4. A compound according to claim 3 wherein Ring B is 3 or 4 monosubstituted or 3,4-disubstituted.

5. A compound according to claim 4 wherein said Ring B substituent is selected from or said Ring B substituents are each independently selected from the group consisting of: halogen; hydroxyl; lower alkoxy; lower alkoxy substituted with hydroxyl or lower alkoxy; —NR$^1$R$^2$; and CF$_3$; wherein R$^1$ and R$^2$ are each independently selected from the group consisting of: hydrogen; lower alkyl; and lower alkyl substituted with hydroxyl or lower alkoxy; and R$^1$ and R$^2$, together with N, can form a 5- or 6-membered heterocyclic ring.

6. A compound according to claim 1 wherein L is a bond and Ring B is an azole substituted by 1 to 4 substituents selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —NR$^1$R$^2$; and said azole is selected from the group consisting of 1,3,4-oxadiazole, 1,2,4-oxadiazole, 1,2,3-triazole, 1,2,4-triazole, and tetrazole.

7. A compound according to claim 6 wherein Ring B is a 1,3,4-oxadiazole.

8. A compound according to claim 1 wherein Ring A is phenyl substituted by methyl at a position that is ortho with relation to 1-alkyl-1H-pyrazolo[3,4-d]pyrimidin-3-yl-methoxy.

9. A compound according to claim 1 wherein R is methyl.

10. A compound according to claim 1 wherein all halogens are selected from the group consisting of Cl and F.

11. A compound according to claim 1 wherein L is selected from the group consisting of —CH$_2$O—, —NHCO—, and —CONH—.

12. A compound according to claim 1 wherein:
Ring A is substituted phenyl;
L is selected from the group consisting of —NHCO—, —CONH—, and —CH$_2$O—; and
Ring B is substituted phenyl.

13. A compound according to claim 1 wherein:
Ring A is selected from the group consisting of phenyl and phenyl substituted by methyl;
L is a bond; and
Ring B is an azole substituted by 1 to 4 substituents selected from the group consisting of: lower alkyl; fluorinated alkyl; aryl-substituted alkyl; hydroxyl; lower alkoxy; lower alkoxy substituted by hydroxyl or lower alkoxy; halogen; cyano; and —NR$^1$R$^2$.

14. A compound according to claim 13 wherein said azole is selected from the group consisting of: 1,3,4-oxadiazole; 1,2,4-oxadiazole; 1,2,3-triazole; 1,2,4-triazole; and tetrazole.

15. A compound according to claim 14 wherein said azole is 1,3,4-oxadiazole.

16. A compound according to claim 1 selected from the group consisting of:
- 3-(3-benzyloxy-phenoxymethyl)-1-methyl-1H-pyrazolo[3,4-d]pyrimidin-4-ylamine;
- N-[3-(4-amino-1-methyl-1H-pyrazolo[3,4-d]pyrimidin-3-ylmethoxy)-4-methyl-phenyl]-3-chloro-4-(2-hydroxy-ethylamino)-benzamide;
- N-[3-(4-amino-1-methyl-1H-pyrazolo[3,4-d]pyrimidin-3-ylmethoxy)-4-methyl-phenyl]-3-chloro-benzamide;
- 4-Amino-1-methyl-3-[2-methyl-5-(3-methyl-[1,2,4]oxadiazol-5-yl)-phenoxymethyl]-1H-pyrazolo[3,4-d]pyrimidine;
- 3-(5-benzyloxy-2-methyl-phenoxymethyl)-1-methyl-1H-pyrazolo[3,4-d]pyrimidin-4-ylamine;
- 3-(4-amino-1-methyl-1H-pyrazolo[3,4-d]pyrimidin-3-ylmethoxy)-N-(4-chloro-phenyl)-4-methyl-benzamide;
- 3-[5-(4-chloro-benzyloxy)-2-methyl-phenoxymethyl]-1-methyl-1H-pyrazolo[3,4-d]pyrimidin-4-ylamine;
- 1-methyl-3-[2-methyl-5-(5-methyl-[1,3,4]oxadiazol-2-yl)-phenoxymethyl]-1H-pyrazolo[3,4-d]pyrimidin-4-ylamine;
- 3-(4-amino-1-methyl-1H-pyrazolo[3,4-d]pyrimidin-3-ylmethoxy)-N-(3-chloro-4-fluoro-phenyl)-4-methyl-benzamide; and
- a pharmaceutically-acceptable salt or ester of any of the foregoing compounds.

17. A pharmaceutical composition comprising a therapeutically-effective amount of a compound according to claim 1 and a carrier.

18. A unit dose formulation comprising a therapeutically-effective amount of a compound according to claim 1 and a carrier.

* * * * *

UNITED STATES PATENT AND TRADEMARK OFFICE
CERTIFICATE OF CORRECTION

| | | |
|---|---|---|
| PATENT NO. | : 7,968,554 B2 | Page 1 of 1 |
| APPLICATION NO. | : 12/175562 | |
| DATED | : June 28, 2011 | |
| INVENTOR(S) | : Bartkovitz et al. | |

It is certified that error appears in the above-identified patent and that said Letters Patent is hereby corrected as shown below:

ON THE TITLE PAGE:

Item (73) Assignee: should read -- Hoffmann-La Roche Inc., Nutley, NJ (US) --.

Signed and Sealed this
Fourth Day of October, 2011

David J. Kappos
*Director of the United States Patent and Trademark Office*